United States Patent [19]

Sasaki

[11] Patent Number: 4,709,096

[45] Date of Patent: Nov. 24, 1987

[54] STILBENE DERIVATIVES, DISTYRYL DERIVATIVES AND ELECTROPHOTOGRAPHIC PHOTOCONDUCTOR COMPRISING AT LEAST ONE OF THE DERIVATIVES

[75] Inventor: Masaomi Sasaki, Susono, Japan

[73] Assignee: Ricoh Company, Ltd., Tokyo, Japan

[21] Appl. No.: 704,675

[22] Filed: Feb. 22, 1985

Related U.S. Application Data

[62] Division of Ser. No. 595,022, Mar. 30, 1984.

[30] Foreign Application Priority Data

| | | | |
|---|---|---|---|
| Apr. 14, 1983 | [JP] | Japan | 58-64526 |
| Apr. 14, 1983 | [JP] | Japan | 58-64527 |
| Apr. 14, 1983 | [JP] | Japan | 58-64528 |
| Apr. 14, 1983 | [JP] | Japan | 58-64529 |

[51] Int. Cl.[4] .................... C07C 87/28; C07C 87/54

[52] U.S. Cl. .................... 564/374; 564/384; 564/433; 564/442; 564/443; 564/305; 558/418; 558/422; 560/43; 560/48; 562/457; 562/458

[58] Field of Search ............... 564/305, 433, 442, 443, 564/374, 384; 548/445; 758/418, 422; 560/43, 48; 562/457, 458

[56] References Cited

U.S. PATENT DOCUMENTS

| | | | |
|---|---|---|---|
| 3,879,463 | 4/1975 | Peters, Jr. et al. | 564/443 |
| 4,451,545 | 5/1984 | Hashimoto et al. | 430/59 |

FOREIGN PATENT DOCUMENTS

58/65440 4/1983 Japan .

OTHER PUBLICATIONS

DuBois, J. E. et al., *Tetrahedron Letters*, No. 20, pp. 1713-1716, (1976).

Beilstein's Handbuck der Organischen Chemie, vol. 5, 1922, pp. 644, 676 and 691.

Beilstein, vol. 5, III.Erg.W., 1965, pp.2159 and 2160.

Beilstein, vol. 5, IV.Erg.W., 1980, p. 2320.

*Primary Examiner*—Charles F. Warren
*Assistant Examiner*—John A. Sopp
*Attorney, Agent, or Firm*—Flynn, Thiel, Boutell & Tanis

[57] ABSTRACT

Stilbene derivatives of the formula (I)

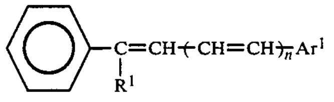

and distyryl derivatives of the formula (II),

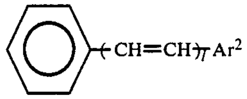

as defined in the specification, and an electrophotographic photoconductor comprising an electroconductive support material and a photosensitive layer overlayed thereon comprising at least one of the above derivatives, are disclosed.

11 Claims, 5 Drawing Figures

STILBENE DERIVATIVES, DISTYRYL DERIVATIVES AND ELECTROPHOTOGRAPHIC PHOTOCONDUCTOR COMPRISING AT LEAST ONE OF THE DERIVATIVES

This is a division of application Ser. No. 595,022 filed Mar. 30, 1984.

BACKGROUND OF THE INVENTION

The present invention relates to stilbene derivatives, distyryl derivatives, and an electrophotographic photoconductor comprising a photosensitive layer containing at least one of those derivatives overlayed on an electroconductive support material.

Conventionally, a variety of inorganic and organic electrophotographic photoconductors are known. As inorganic photoconductors for use in electrophotography, there are known types, in which the photoconductive material is, for instance, selenium, cadmium sulfide and zinc oxide. In an electrophotographic process, a photoconductor is first exposed to corona charges in the dark, so that the surface of the photoconductor is electrically charged uniformly. The thus uniformly charged photoconductor is then exposed to original light images and the portions exposed to the original light images selectively become electroconductive so that electric charges dissipate from the exposed portions of the photoconductor, whereby latent electrostatic images corresponding to the original light images are formed on the surface of the photoconductor. The latent electrostatic images are then developed by the so-called toner which comprises a colorant, such as a dye or a pigment, and a binder agent made, for instance, of a polymeric material; thus, visible developed images can be obtained on the photoconductor. It is necessary that photoconductors for use in electrophotography have at least the following fundamental properties: (1) chargeability to a predetermined potential in the dark; (2) minimum electric charge dissipation in the dark; and (3) quick dissipation of electric charges upon exposure to light.

While the above-mentioned inorganic electrophotographic photoconductors have many advantages over other conventional electrophotographic photoconductors, at the same time they have several shortcomings from the viewpoint of practical use.

For instance, a selenium photoconductor, which is widely used at present, has the shortcoming that its production is different and, accordingly, its production cost is high. Further, it is difficult to work it into the form of a belt due to its poor flexibility, and it is so vulnerable to heat and mechanical shocks that it must be handled with the utmost care.

Cadmium sulfide photoconductors and zinc oxide photoconductors are prepared by dispersing cadmium sulfide or zinc oxide in a binder resin. They can be produced inexpensively compared with selenium photoconductors and are also used commonly in practice. However, the cadmium sulfide and zinc oxide photoconductors are poor in surface smoothness, hardness, tensile strength and wear resistance. Therefore, they are not suitable as photoconductors for use in plain paper copiers in which the photoconductors are used in quick repetition.

Recently, organic electrophotographic photoconductors, which are said not to have the shortcomings of the inorganic electrophotographic photoconductors, have been proposed, and some of them are in fact employed for practical use. Representative examples of such organic electrophotographic photoconductors are an electrophotographic photoconductor comprising poly-N-vinylcarbazole and 2,4,7-trinitro-fluorene-9-one (U.S. Pat. No. 3,484,237); a photoconductor in which poly-N-vinylcarbazole is sensitized by a pyrylium salt type coloring material (Japanese Patent Publication No. 48-25658); a photoconductor containing as the main component an organic pigment (Japanese Laid-Open Patent Application No. 47-37543); and a photoconductor containing as the main component a eutectic crystaline complex (Japanese Laid-Open Patent Application No. 47-10735).

Although the above-mentioned organic electrophotographic photoconductors have many advantages over other conventional electrophotographic photoconductors, they still have several shortcomings from the viewpoint of practical use, in particular, for use in high speed copying machines, in terms of cost, production, durability and electrophotographic sensitivity.

SUMMARY OF THE INVENTION

It is therefore an object of the present invention to provide stilbene derivatives, distyryl derivatives and an electrophotographic photoconductor or element comprising a photosensitive layer containing at least one of those derivatives overlayed on an electroconductive support material, with high photosensitivity, which does not give rise to difficulties in producing the electrophotographic photoconductor, and which is comparatively inexpensive and excellent in durability.

The stilbene derivatives employed in the present invention are represented by the following general formula (I):

(I)

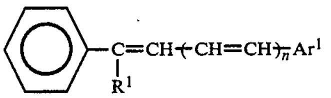

wherein $R^1$ represents an alkyl group or an aralkyl group, $Ar^1$ represents an unsubstituted or substituted naphthyl group, an unsubstituted or substituted anthryl group, or

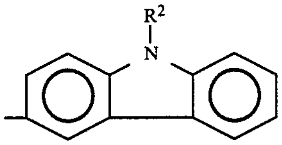

(in which $R^2$ represents an alkyl group or an unsubstituted or substituted phenyl group), or

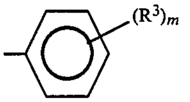

(in which $R^3$ represents hydrogen, an alkyl group, an alkoxy group, an alkylenedioxy group, halogen or a substituted amino group represented by

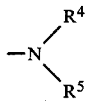

wherein $R^4$ and $R^5$ each represent an alkyl grooup, an unsubstituted or substituted aralkyl group, or an unsubstituted or substituted aryl group, m is an integer of 1, 2 or 3, and when m is an integer of 2 or 3, $R^3$'s may be the same or different), and n is an integer of 0 or 1.

The distyryl derivatives employed in the present invention are represented by the following general formula (II):

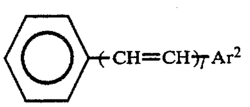

(II)

wherein $Ar^2$ represents an unsubstituted or substituted naphthyl group,

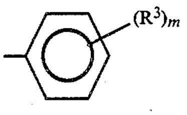

(in which $R^3$ represents hydrogen, an alkyl group, an alkoxy group, an alkylenedioxy group, halogen or a substituted amino group represented by

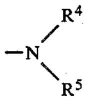

wherein $R^4$ and $R^5$ each represent an alkyl group, an unsubstituted or substituted aralkyl group, or an unsubstituted or substituted aryl group, m is an integer of 1, 2, or 3, and when m is an integer of 2 or 3, $R^3$'s may be the same or different), and l is an integer of 2 or 3.

DETAILED DESCRIPTION OF THE PREFERRED EMBODIMENTS

In the electrophotographic photoconductor according to the present invention, at least one stilbene derivative of the previously described formula (I) or one distyryl derivative of the formula (II) is contained in the photosensitive layer. The stilbene derivatives and the distyryl derivatives can be employed in different ways, for example, as shown in FIG. 1, FIG. 2 and FIG. 3.

Figure 1:
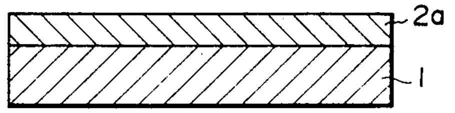
FIG. 1 is an enlarged schematic cross-sectional view of an embodiment of an electrophotographic photoconductor according to the present invention.

In the photoconductor shown in FIG. 1, a photosensitive layer **2*a* is formed on an electroconductive support material 1, which photosensitive layer 2*a*** comprises a stilbene derivative or a distyryl derivative, a sensitizer dye and a binder agent. In this photoconductor, the stilbene derivative and the distyryl derivative work as photoconductor material through which charge carriers are generated and transported. The generation and transportation of charge carrier are necessary for the light decay of the photoconductor. However, the stilbene derivatives and the distyryl derivatives scarcely absorb light in the visible light range and, therefore, it is necessary to sensitize those derivatives by addition thereto of a sensitizer dye which absorbs light in the visible light range in order to form latent electrostatic images on the photoconductor by use of visible light.

Figure 2:
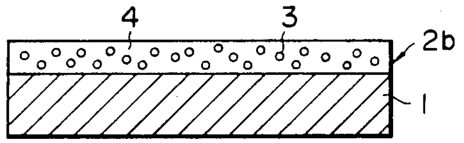
FIG. 2 is an enlarged schematic cross-sectional view of another embodiment of an electrophotographic photoconductor according to the present invention.
Figure 3:
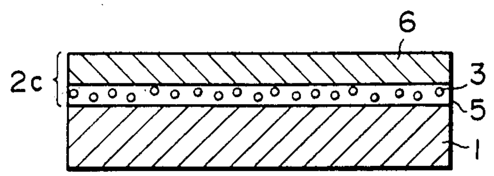
FIG. 3 is an enlarged schematic cross-sectional view of a further embodiment of an electrophotographic photoconductor according to the present invention.

Referring to FIG. 2, there is shown an enlarged cross-sectional view of another embodiment of an electrophotographic photoconductor according to the present invention.

In the figure, on the electroconductive support material 1, there is formed a photosensitive layer **2*b* comprising a charge generating material 3 dispersed in a charge transporting medium 4 which comprises a stilbene derivative or a distyryl derivative and a binder agent. In this embodiment, the stilbene derivative or distyryl derivative and the binder agent in combination constitute the charge transporting medium 4. The charge generating material 3, which is, for example, an inorganic or organic pigment, generates charge carriers. The charge transporting medium 4 mainly serves to accept the charge carriers generated by the charge generating material 3** and to transport those charge carriers.

In this electrophotographic photoconductor, it is a basic requirement that the light-absorption wavelength regions of the charge generating material 3 and the stilbene derivative and the distyryl derivative not overlap in the visible light range. This is because, in order that the charge generating material 3 produce charge carriers efficiently, it is necessary that light pass through the charge transporting medium 4 and reach the surface of the charge generating material 3. Since the stilbene derivatives of the formula (I) and the distyryl derivatives of the formula (II) do not substantially absorb light in the visible range, they can work effectively as charge transporting materials in combination with the charge generating material 3 which absorbs the light in the visible region and generates charge carriers.

Referring to FIG. 3, there is shown an enlarged cross-sectional view of a further embodiment of an electrophotographic photoconductor according to the present invention. In the figure, there is formed on the electroconductive support material 1 a two-layered photosensitive layer **2*c* comprising a charge generating layer 5 consisting essentially of the charge generating material 3, and a charge transporting layer 6** containing a stilbene derivative of the formula (I) or a distyryl derivative of the formula (II).

In this photoconductor, light which has passed through the charge transporting layer 6 reaches the charge generating layer 5, so that charge carriers are generated within the charge generating layer 5 in the region which the light has reached. The charge carriers which are necessary for the light decay for latent electrostatic image formation are generated by the charge generating material 3, accepted and transported by the charge transporting layer 6. In the charge transporting layer 6, the stilbene derivative or the distyryl derivative works mainly by accepting and transporting charge carriers. The generation and transportation of the charge carriers are performed in the same manner as that in the photoconductor shown in FIG. 2.

The stilbene derivatives of the formula (I) for use in the present invention can be prepared by reacting a phenyl derivative of formula (Ia) with an aldehyde derivative of formula (Ib) in the presence of a basic catalyst at temperatures ranging from room temperature to about 100° C.:

(I)

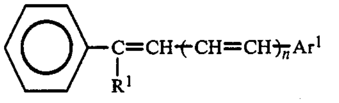

(Ia)

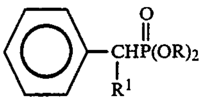

wherein $R^1$ represents an alkyl group or an aralkyl group, and R represents a lower alkyl group.

$OHC—CH=CH)_nAr^1$ (Ib)

wherein $Ar^1$ represents an unsubstituted or substituted naphthyl group, an unsubstituted or substituted anthryl group, or

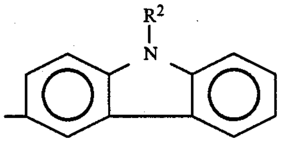

(in which $R^2$ represents an alkyl group or an unsubstituted or substituted phenyl group), or

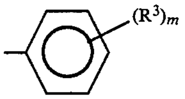

(in which $R^3$ represents hydrogen, an alkyl group, an alkoxy group, an alkylenedioxy group, halogen or a substituted amino group represented by

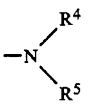

wherein $R^4$ and $R^5$ each represent an alkyl group, an unsubstituted or substituted aralkyl group, or an unsubstituted or substituted aryl group, m is an integer of 1, 2 or 3, and when m is an integer of 2 or 3, $R^3$'s may be the same or different), and n is an integer of 0 or 1.

In the above formula (I), the substituents of the naphthyl group represented by $Ar^1$ are, for example, an alkyl group, an alkoxy group, halogen, a substituted amino group, and the substituents of the aralkyl group or aryl group represented by $R^4$ and $R^5$ are, for example, an alkyl group, an alkoxy group, a thioalkoxy group, a thiophenoxy group, halogen, a dialkylamino group, a hydroxy group, a carboxyl group, and an ester group thereof, an acyl group, an allyloxy group, an aralkyloxy group, a trihalomethyl group and a cyano group.

The distyryl derivatives of the formula (II) for use in the present invention can be prepared by reacting a phenyl derivative of formula (IIa) with an aldehyde derivative of formula (IIb) in the presence of a basic catalyst at temperatures ranging from room temperature to about 100° C.

(II)

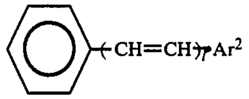

(IIa)

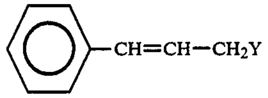

wherein Y represents a triphenylphosphonium group of the formula

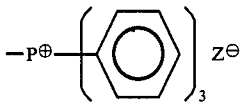

in which $Z^{\ominus}$ indicates a halogen ion; or a dialkoxyphosphorous group of the formula $—PO(OR)_2$ in which R indicates a lower alkyl group.

$Ar^2—CH=CH)_pCHO$ (IIb)

wherein $Ar^2$ is the same as that defined in the previously described general formula (II), and p is an integer of 0 or 1.

In the above formula (II), the substituents of the naphthyl group represented by $Ar^2$ are, for example, an alkyl group, an alkoxy group, halogen and a substituted amino group, and the substituents of the aralkyl group or aryl group represented by $R^4$ and $R^5$ are, for example, an alkyl group, an alkoxy group, a thioalkoxy group, a thiophenoxy group, halogen, a dialkylamino group, a hydroxy group, a carboxyl group, and an ester group thereof, an acyl group, an aryl group, an allyloxy group, an aralkyloxy group, a trihalomethyl group, a nitro group and a cyano group.

Preparation of the stilbene derivatives of the previously described formula (I) will now be explained.

In this preparation, the phenyl derivative of the formula (Ia) can be prepared without difficulty by heating a corresponding halomethyl compound and a trialkyl phosphite without any solvent or in a solvent, such as toluene or xylene. As the trialkyl phosphite, those having alkyl groups with 1 to 4 carbon atoms, in particular, those having methyl groups or ethyl groups are preferable.

The thus prepared phenyl derivative of the formula (Ia) is allowed to react with the aldehyde derivative of the formula (Ib) in the presence of a basic catalyst at temperatures ranging from room temperature to about 100° C.

As the basic catalyst for the above reaction, sodium hydroxide, potassium hydroxide, sodium amide, sodium hydride, and alcoholates such as sodium methylate and potassium tert-butoxide, can be employed.

As the reaction solvent, the following can be employed: methanol, ethanol, isopropanol, butanol, 2-methoxyethanol, 1,2-dimethoxyethane, bis(2-methoxyethyl)ether, dioxane, tetrahydrofuran, toluene, xylene, dimethyl sulfoxide, N,N-dimethylformamide, N-methylpyrrolidone and 1,3-dimethyl-2-imidazolidinone.

Of the above solvents, polar solvents, for example, N,N-dimethylformamide and dimethyl sulfoxide are particularly suitable for this reaction.

The reaction temperature for the above reaction can be set in a relatively wide range, depending upon (i) the stability of the solvent employed in the presence of the basic catalyst, (ii) the reactivities of the condensation components, that is, the phenyl derivative of the formula (Ia) and the aldehyde derivative of the formula (Ib), and (iii) the properties of the basic catalyst which works as a condensation agent in this reaction. When, for example, a polar solvent is employed as the reaction solvent, the reaction temperature can be set in the range of room temperature to about 100° C., more preferably in the range of room temperature to about 80° C. However, if it is desired to shorten the reaction time or when a less reactive condensation agent is employed, the reaction temperature can be elevated beyond the aforementioned range.

Preparation of stilbene derivatives of the formula (I) will now be explained in detail by referring to the following examples:

SYNTHESIS EXAMPLE 1-1 (SYNTHESIS OF STILBENE DERIVATIVE COMPOUND NO. 1-26 IN TABLE 3)

2.42 g (0.01 mol) of diethyl α-methylbenzylphosphonate and 2.73 g (0.01 mol) of 4-N,N-diphenylaminobenzaldehyde were dissolved in 15 ml of N,N-dimethyl-formamide. To this mixture, 1.35 g of potassium tert-butoxide was added with the temperature of the reaction mixture maintained in the range of 22° C. to 35° C. After the addition of the potassium tert-butoxide, the reaction mixture was stirred at room temperature for 7 hours and was then diluted with 50 ml of water. An oily material was formed, which was extracted with toluene. The toluene layer portion was washed with water and was then dried. The toluene was removed by evaporation from the toluene layer portion, whereby yellow crystals were obtained. The yield was 3.04 g (84.0%) and the melting point of the product was at 96.5°-99.5° C. The thus obtained yellow crystals were recrystallized from ethanol, whereby α-methyl-4'-N,N-diphenyl-aminostilbene (Compound No. 1-26 in Table 3) was obtained as yellow needle-like crystals. The melting point of the product was at 158.5°-160.5° C.

The results of the elemental analysis of the thus obtained α-methyl-4'-N,N'-diphenylaminostilbene were as follows:

| | % C | % H | % N |
|---|---|---|---|
| Found | 89.87 | 6.42 | 3.82 |
| Calculated | 89.70 | 6.43 | 3.88 |

The above calculation was based on the formula for α-methyl-4'-N,N-diphenylaminostilbene of $C_{27}H_{23}N$.

Figure 4:
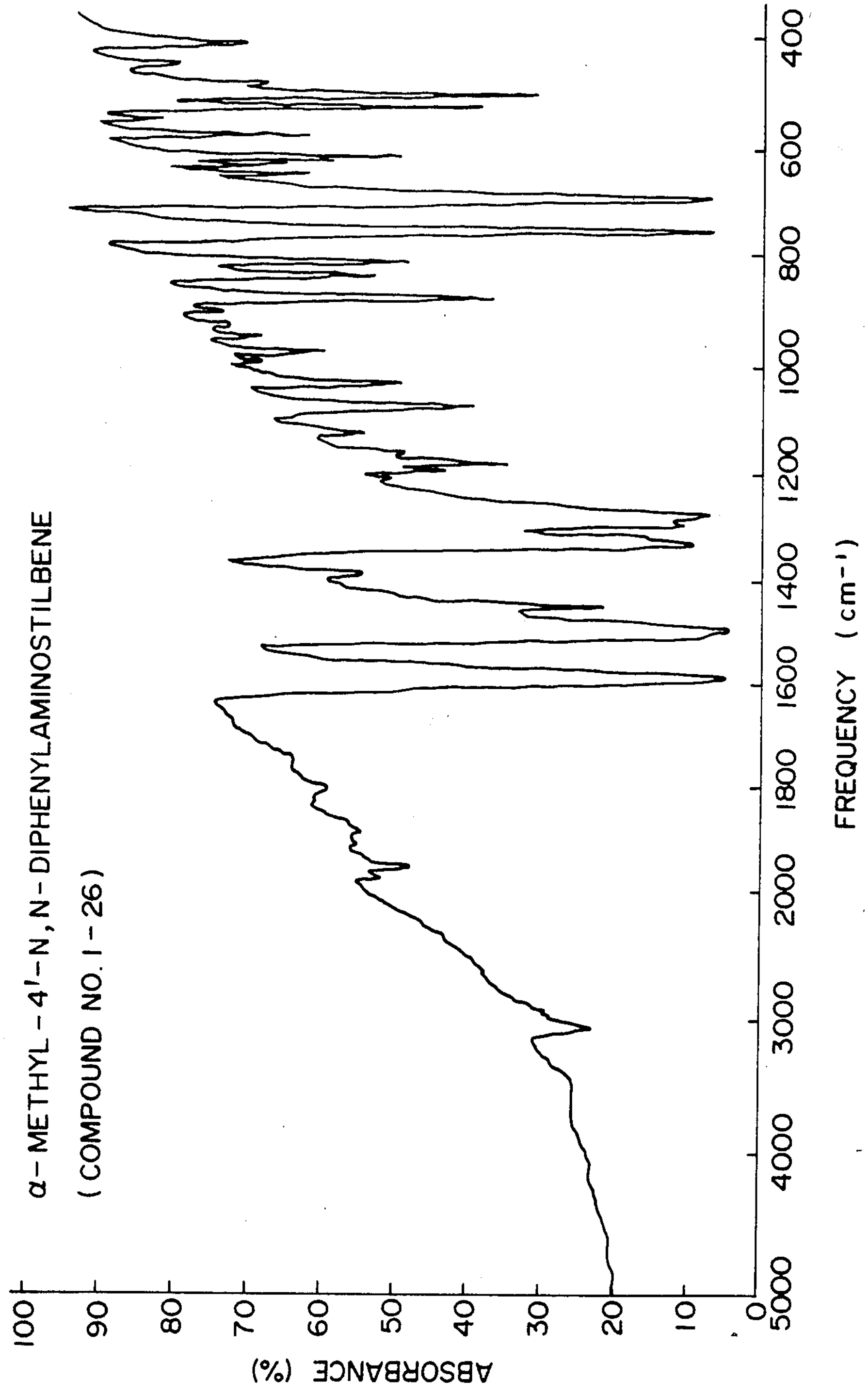
FIG. 4 is an infrared spectrum of α-methyl-4'-N,N-diphenylaminostilbene, which is Stilbene Derivative Compound No. 1-26 in Table 3.

An infrared spectrum of the α-methyl-4'-N,N-diphenylaminostilbene, taken by use of a KBr pellet, indicated a peak at 970 $cm^{-1}$ characteristic of the out-of-plane =CH (trans) deformation vibrations as shown in FIG. 4.

SYNTHESIS EXAMPLES 1-2 THROUGH 1-11

Synthesis Example 1'-1 was repeated except that 4-N,N-diphenylaminobenzaldehyde employed in the Synthesis Example 1-1 was replaced by the respective aldehydes listed in Table 1, whereby the novel stilbene derivatives listed in Table 1 were obtained.

The melting points and the results of the elemental analyses of the above stilbene derivatives prepared in Synthesis Examples 1-2 through 1-11 are in the following Table 2.

TABLE 1

| Synthesis Example No. | Aldehyde | Stilbene Derivative | Stilbene Derivative No. in Table 3 |
|---|---|---|---|
| 1-2 | 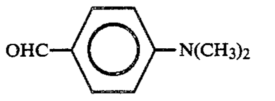 | 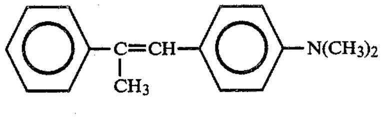 | 17 |
| 1-3 | 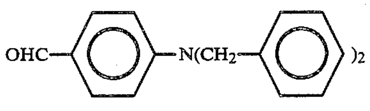 | 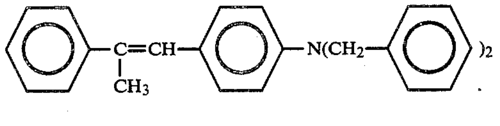 | 18 |
| 1-4 | 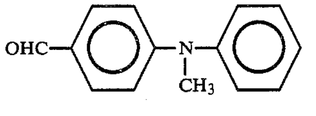 | 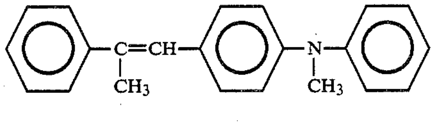 | 70 |

TABLE 1-continued

| Synthesis Example No. | Aldehyde | Stilbene Derivative | Stilbene Derivative No. in Table 3 |
|---|---|---|---|
| 1-5 | 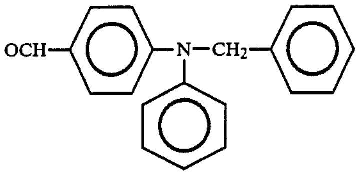 | 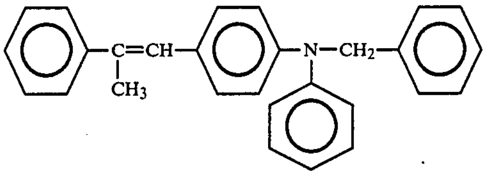 | 65 |
| 1-6 | 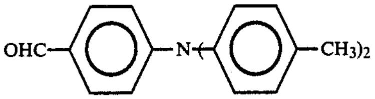 | 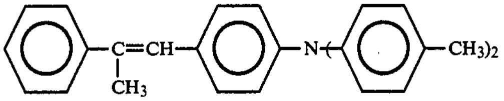 | 32 |
| 1-7 | 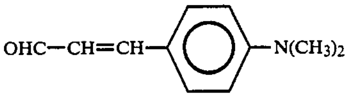 | 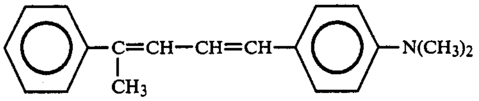 | 16 |
| 1-8 | 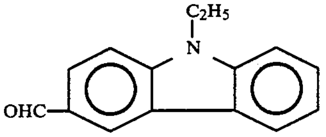 | 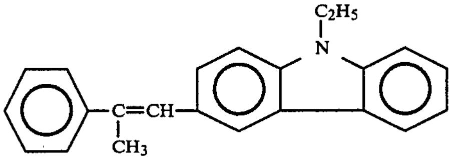 | 4 |
| 1-9 | 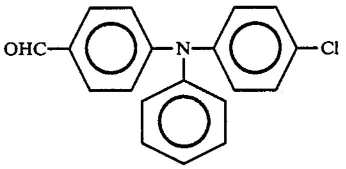 | 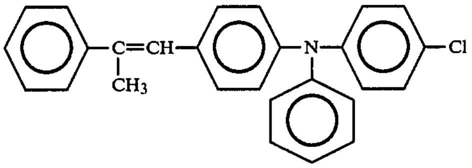 | 41 |
| 1-10 | 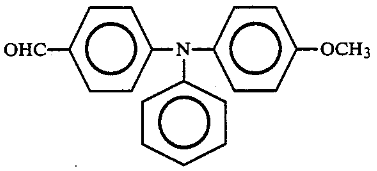 | 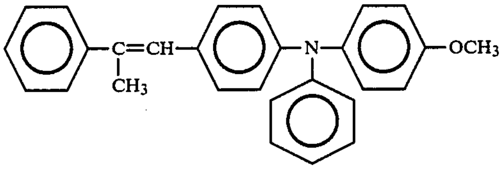 | 40 |
| 1-11 | 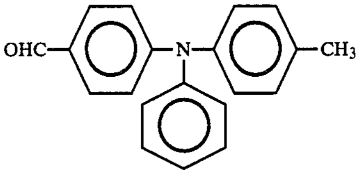 | 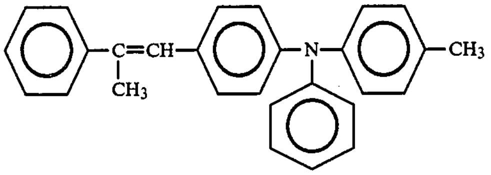 | 37 |

TABLE 2

| Synthesis Example No. | Melting Point (°C.) | Elemental Analysis Found/Calculated % C | % H | % N |
|---|---|---|---|---|
| 1-2 | 102.0~103.0 | 86.00/86.01 | 8.21/8.08 | 5.98/5.90 |
| 1-3 | 121.0~122.0 | 89.31/89.40 | 7.10/7.00 | 3.69/3.60 |
| 1-4 | 79.5~80.0 | 88.34/88.24 | 7.07/7.08 | 4.79/4.68 |
| 1-5 | 126.0~127.0 | 89.52/89.55 | 6.75/6.72 | 3.81/3.73 |
| 1-6 | 103.5~104.5 | 89.44/89.40 | 7.01/7.00 | 3.62/3.60 |
| 1-7 | 170.0~170.5 | 86.65/86.63 | 8.15/8.05 | 5.37/5.32 |
| 1-8 | 107.5~108.5 | 88.64/88.69 | 6.91/6.81 | 4.55/4.50 |
| 1-9 | 114.0~115.5 | 81.92/81.90 | 5.52/5.61 | 3.56/3.54 |
| 1-10 | 92.0~93.0 | 85.81/85.89 | 6.39/6.45 | 3.60/3.58 |
| 1-11 | Oily Product | 89.40/89.55 | 6.54/6.72 | 3.69/3.73 |

In addition to the stilbene derivatives described in Synthesis Examples 1-1 through 1-11, other stilbene derivatives of the formula (I), listed in the following Table 3, are also useful in the present invention:

(I)

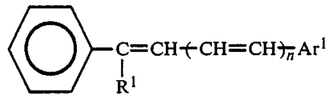

TABLE 3
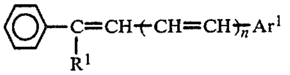
| Compound No. | $R^1$ | n | $Ar^1$ |
|---|---|---|---|
| 1-1 | $-CH_3$ | 0 | 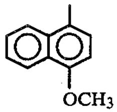 |
| 1-2 | $-CH_3$ | 0 | 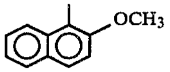 |
| 1-3 | $-CH_3$ | 0 | 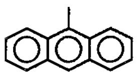 |
| 1-4 | $-CH_3$ | 0 | 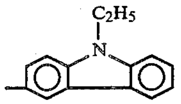 |
| 1-5 | 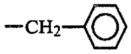 | 0 | 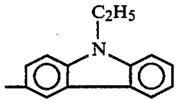 |
| 1-6 | $-CH_3$ | 0 | 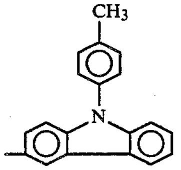 |
| 1-7 | 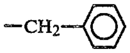 | 1 | 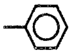 |
| 1-8 | 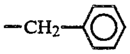 | 1 | 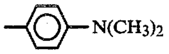 |
| 1-9 | 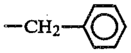 | 1 | 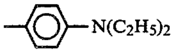 |
| 1-10 | $-CH_3$ | 0 | 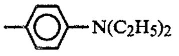 |
| 1-11 | 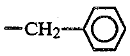 | 0 | 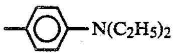 |
| 1-12 | $-CH_3$ | 0 | 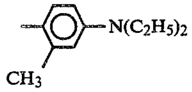 |
| 1-13 | $-CH_3$ | 0 | 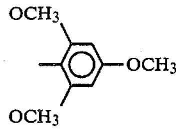 |
TABLE 3-continued
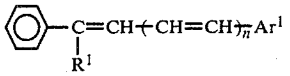
| Compound No. | $R^1$ | n | $Ar^1$ |
|---|---|---|---|
| 1-14 | $-CH_3$ | 0 | 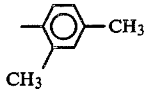 |
| 1-15 | $-CH_3$ | 1 | 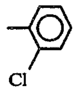 |
| 1-16 | $-CH_3$ | 1 | 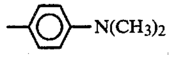 |
| 1-17 | $-CH_3$ | 0 | 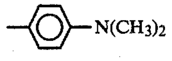 |
| 1-18 | $-CH_3$ | 0 | 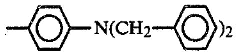 |
| 1-19 | $-CH_3$ | 0 | 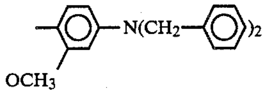 |
| 1-20 | $-CH_3$ | 0 | 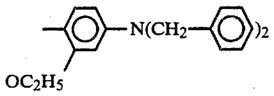 |
| 1-21 | $-CH_3$ | 0 | 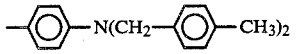 |
| 1-22 | $-CH_3$ | 0 | 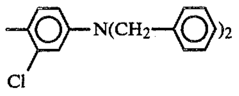 |
| 1-23 | $-CH_3$ | 0 | 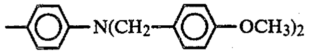 |
| 1-24 | $-CH_3$ | 0 | 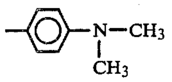 |
| 1-25 | $-CH_3$ | 0 | 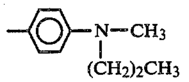 |
| 1-26 | $-CH_3$ | 0 | 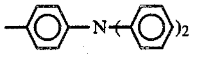 |
| 1-27 | $-C_2H_5$ | 0 | 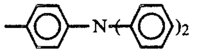 |
| 1-28 | $-C_3H_7(n)$ | 0 | 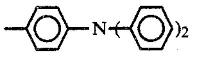 |

TABLE 3-continued
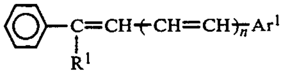
| Compound No. | $R^1$ | n | $Ar^1$ |
|---|---|---|---|
| 1-29 | $-C_3H_7(i)$ | | 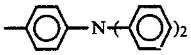 |
| 1-30 | $-C_4H_3(n)$ | 0 | 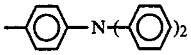 |
| 1-31 | 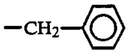 | 0 | 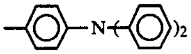 |
| 1-32 | $-CH_3$ | 0 | 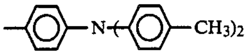 |
| 1-33 | $-C_2H_5$ | 0 | 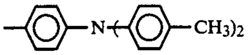 |
| 1-34 | 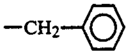 | 0 | 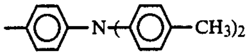 |
| 1-35 | $-CH_3$ | 0 | 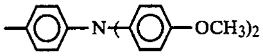 |
| 1-36 | $-CH_3$ | 0 | 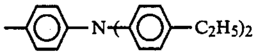 |
| 1-37 | $-CH_3$ | 0 | 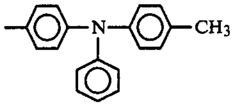 |
| 1-38 | $-C_2H_5$ | 0 | 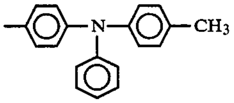 |
| 1-39 | 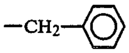 | 0 | 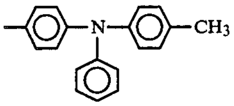 |
| 1-40 | $-CH_3$ | 0 | 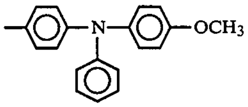 |
| 1-41 | $-CH_3$ | 0 | 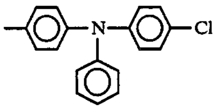 |
| 1-42 | $-CH_3$ | 0 | 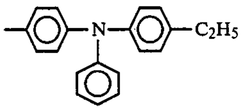 |
TABLE 3-continued
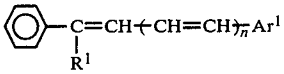
| Compound No. | $R^1$ | n | $Ar^1$ |
|---|---|---|---|
| 1-43 | $-CH_3$ | 0 | 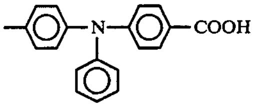 |
| 1-44 | $-CH_3$ | 0 | 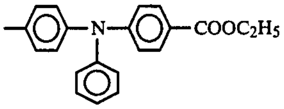 |
| 1-45 | $-CH_3$ | 0 | 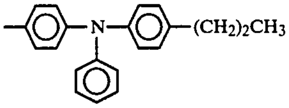 |
| 1-46 | $-CH_3$ | 0 | 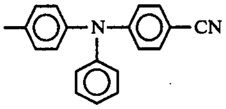 |
| 1-47 | $-CH_3$ | 0 | 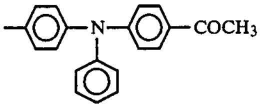 |
| 1-48 | $-CH_3$ | 0 | 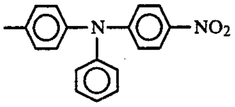 |
| 1-49 | $-CH_3$ | 0 | 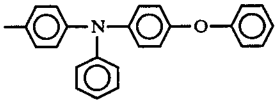 |
| 1-50 | $-CH_3$ | 0 | 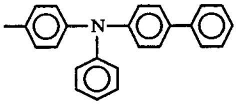 |
| 1-51 | $-CH_3$ | 0 | 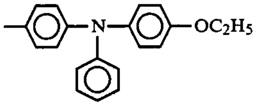 |
| 1-52 | $-CH_3$ | 0 | 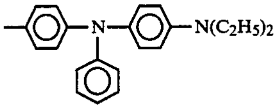 |
| 1-53 | $-CH_3$ | 0 | 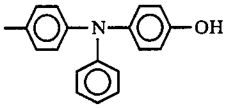 |

TABLE 3-continued

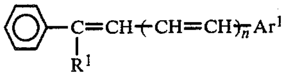

| Compound No. | $R^1$ | n | $Ar^1$ |
|---|---|---|---|
| 1-54 | $-CH_3$ | 0 | 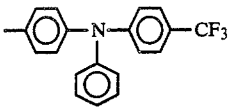 |
| 1-55 | $-CH_3$ | 0 | 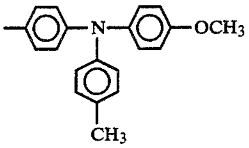 |
| 1-56 | $-CH_3$ | 0 | 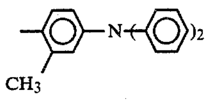 |
| 1-57 | $-CH_3$ | 0 | 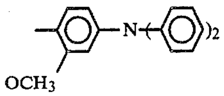 |
| 1-58 | $-CH_3$ | 0 | 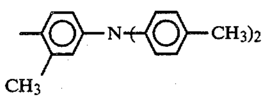 |
| 1-59 | $-CH_3$ | 0 | 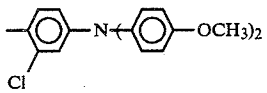 |
| 1-60 | $-CH_3$ | 0 | 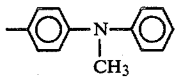 |
| 1-61 | $-CH_3$ | 0 | 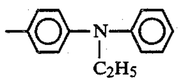 |
| 1-62 | $-CH_3$ | 0 | 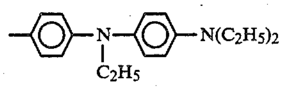 |
| 1-63 | $-C_2H_5$ | 0 | 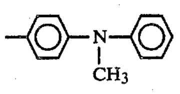 |
| 1-64 | $-C_2H_5$ | 0 | 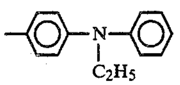 |
| 1-65 | $-CH_3$ | 0 | 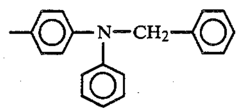 |

TABLE 3-continued

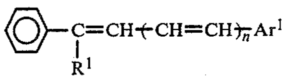

| Compound No. | $R^1$ | n | $Ar^1$ |
|---|---|---|---|
| 1-66 | $-C_2H_5$ | 0 | 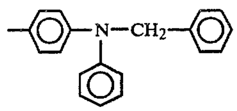 |
| 1-67 | $-CH_3$ | 0 | 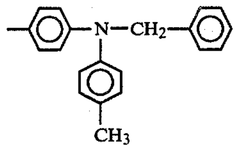 |
| 1-68 | $-CH_3$ | 0 | 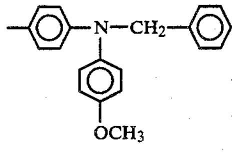 |
| 1-69 | $-CH_3$ | 0 | 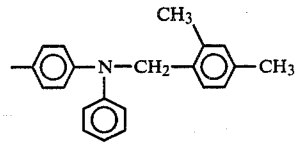 |
| 1-70 | $-CH_3$ | 0 | 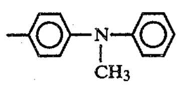 |

Preparation of the distyryl derivatives of the previously described formula (II) will now be explained.

In this preparation, the phenyl derivative of the formula (IIa) can be prepared without difficulty by heating a corresponding halomethyl compound and a trialkyl phosphite or triphenylphosphite without any solvent or in a solvent, such as toluene, tetrahydrofuran, or N,N-dimethylformamide. As the trialkyl phosphite, those having alkyl groups with 1 to 4 carbon atoms, in particular, those having methyl groups or ethyl groups are preferable.

The thus prepared phenyl derivative of the formula (IIa) is allowed to react with the aldehyde derivative of the formula (IIb) in the presence of a basic catalyst at temperatures ranging from room temperature to about 100° C.

As the basic catalyst for the above reaction, sodium hydroxide, potassium hydroxide, sodium amide, sodium hydride, and alcoholates such as sodium methylate and potassium tert-butoxide, can be employed.

As the reaction solvent, the following can be employed: methanol, ethanol, isopropanol, butanol, 2-methoxyethanol, 1,2-dimethoxyethane, bis(2-methoxyethyl)ether, dioxane, tetrahydrofuran, toluene, xylene, dimethyl sulfoxide, N,N-dimethylformamide, N-methylpyrrolidone and 1,3-dimethyl-2-imidazolidinone.

Of the above solvents, polar solvents, for example, N,N-dimethylformamide and dimethyl sulfoxide are particularly suitable for this reaction.

The reaction temperature for the above reaction can be set in a relatively wide range, depending upon (i) the stability of the solvent employed in the presence of the basic catalyst, (ii) the reactivities of the condensation components, that is, the phenyl derivative of the formula (IIa) and the aldehyde derivative of the formula (IIb), and (iii) the properties of the basic catalyst which works as a condensation agent in this reaction. When, for example, a polar solvent is employed as the reaction solvent, the reaction temperature can be set in the range of room temperature to about 100° C., more preferably in the range of room temperature to about 80° C. However, if it is desired to shorten the reaction time or when a less reactive condensation agent is employed, the reaction temperature can be elevated beyond the aforementioned range.

SYNTHESIS EXAMPLE 2-1 (SYNTHESIS OF DISTYRYL DERIVATIVE NO. 2-27 IN TABLE 6)

5.09 g (0.02 mol) of trans-diethylcinnamylphosphonate and 5.47 g (0.02 mol) of 4-N,N-diphenylaminobenzaldehyde were dissolved in 40 ml of N,N-dimethylformamide. To this mixture, 4.63 g of a 28% methanol solution of sodium methylate was added dropwise over a period of 40 minutes at temperatures ranging from 27° C. to 35° C. After the addition of the methanol solution of sodium methylate, the reaction mixture was stirred at room temperature for 3 hours and then diluted with 60 ml of methanol. Crystals separated from the reaction mixture, which were separated by filteration, washed with water, and dried. Thus, yellow crystals were obtained with a yield of 6.20 g (83.0%). The melting point of the thus obtained crystals was at 157.5°-159.0° C.

The crystals were recrystallized from a mixed solvent of dioxane and ethanol in the presence of a small amount of iodine, whereby 1-phenyl-4-(4'-N,N-diphenylaminophenyl)-1,3-butadiene (Compound No. 2-27 in Table 6) was obtained as yellow needle-like crystals. The melting point of the thus obtained 1-phenyl-4-(4'-N,N-diphenylaminophenyl)-1,3-butadiene was at 158.5°-160.5° C.

The results of the elemental analysis thereof were as follows:

| | % C | % H | % N |
|---|---|---|---|
| Found | 90.16 | 6.22 | 3.84 |
| Calculated | 90.03 | 6.22 | 3.75 |

The above calculation was based on the formula for 1-phenyl-4-(4'-N,N-diphenylaminophenyl)-1,3-butadiene of $C_{28}H_{23}N$.

Figure 5:
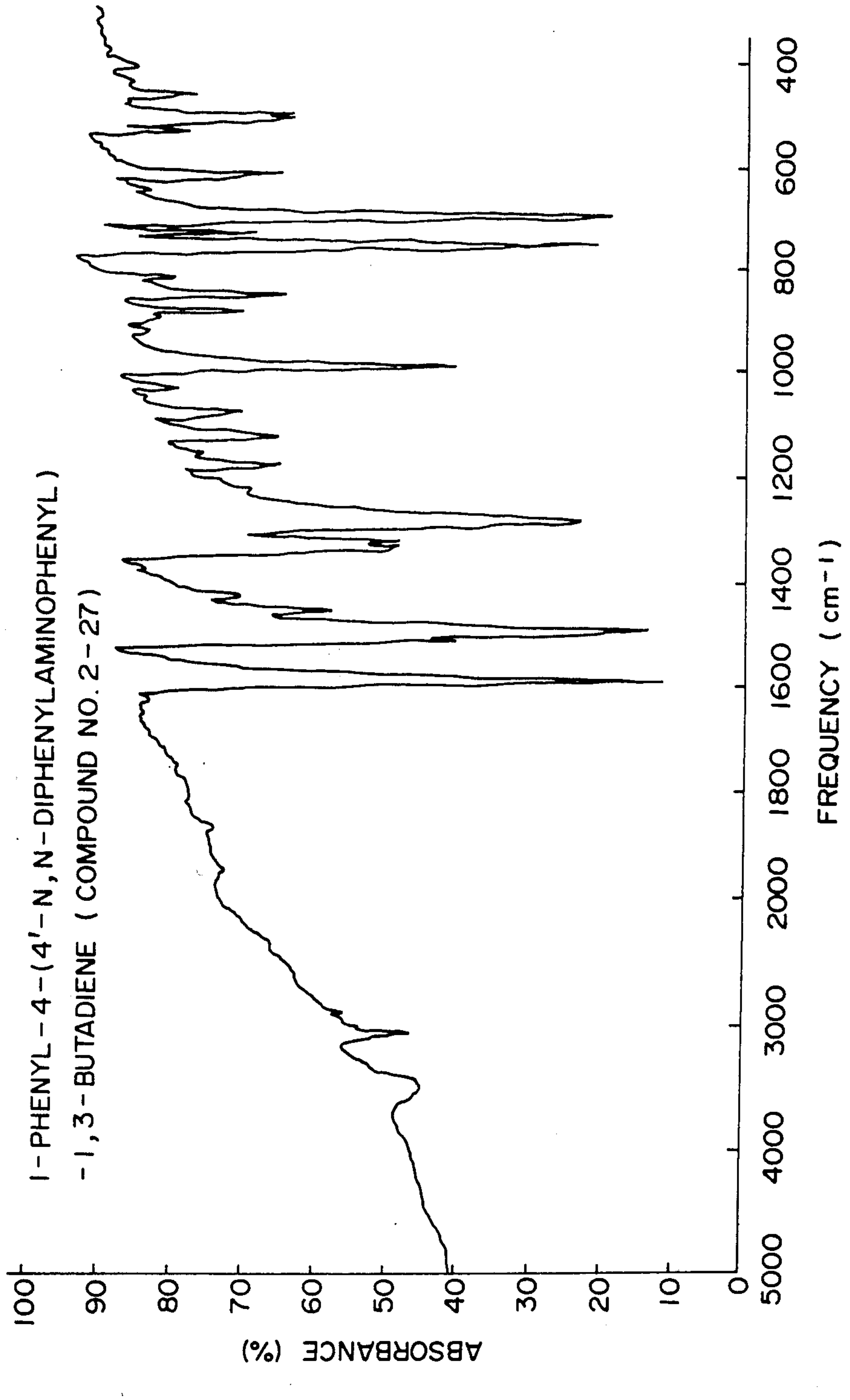
FIG. 5 is an infrared spectrum of 1-phenyl-4-(4'-N,N-diphenylaminophenyl)-1,3-butadiene, which is Distyryl Derivative Compound No. 2-27 in Table 6.

An infrared spectrum of the 1-phenyl-4-(4'-N,N-diphenylaminophenyl)-1,3-butadiene, taken by use of a KBr pellet, indicated a peek at 985 $cm^{-1}$ characteristic of the out-of-plane =CH (trans) deformation vibrations as shown in FIG. 5.

SYNTHESIS EXAMPLE 2-2

8.30 g (0.02 mol) of trans-triphenylphosphoniumcinnamyl chloride and 5.47 g (0.02 mol) of 4-N,N-diphenylaminobenzylaldehyde were dissolved in 40 ml of N,N-dimethylformamide. To this mixture, 4.63 g of a 28% methanol solution of sodium methylate was added dropwise at temperatures ranging from 25° C. to 30° C. over a period of 30 minutes. After the dropwise addition of the methanol solution of sodium methylate, the reaction mixture was stirred at room temperature for 4 hours. The reaction mixture was then diluted with 40 ml of water. Crystals separated from the reaction mixture, which were washed with water, then with methanol, and were then dried.

The thus obtained crystals were recrystallized from a mixed solvent of toluene and n-hexane in the presence of a small amount of iodine, whereby 5.08 g (68.0%) of 1-phenyl-4-(4'-N,N-diphenylaminophenyl)-1,3-butadiene (Distyryl Derivative No. 2-27 in Table 6) was obtained as yellow needle-like crystals. The melting point of the product was at 157.5°-159.5° C.

The result of the elemental analysis of the thus obtained 1-phenyl-4-(4'-N,N-diphenylaminophenyl)-1,3-butadiene were as follows:

| | % C | % H | % N |
|---|---|---|---|
| Found | 90.12 | 6.19 | 3.82 |
| Calculated | 90.03 | 6.22 | 3.75 |

The above calculation was based on the formula for 1-phenyl-4-(4'-N,N-diphenylaminophenyl)-1,3-butadiene of $C_{28}H_{23}N$.

An infrared spectrum of the above synthesized 1-phenyl-4-(4'-N,N-diphenylaminophenyl)-1,3-butadiene, taken by use of a KBr pellet, was identical with the infrared spectrum obtained in Synthesis Example 2-1 as shown in FIG. 5.

SYNTHESIS EXAMPLES 2-3 THROUGH 2-12

Synthesis Example 2-1 was repeated except that the 4-N,N-diphenylbenzaldehyde employed in Synthesis Example 2-1 was replaced by the aldehydes as listed in Table 4, whereby novel distyryl derivatives listed in Table 4 were prepared.

The melting points and the results of the elemental analyses of the above distyryl derivatives prepared in Synthesis Examples 2-3 through 2-12 are shown in Table 5.

TABLE 4

| Synthesis Example No. | Aldehyde | Distyryl Derivative | Compound No. in Table 6 |
|---|---|---|---|
| 2-3 | 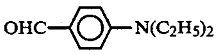 | 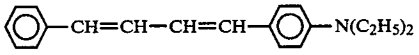 | 2-11 |
| 2-4 | 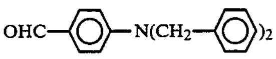 | 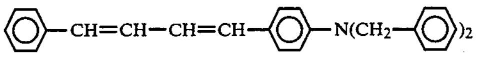 | 2-14 |
| 2-5 | 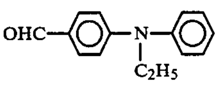 | 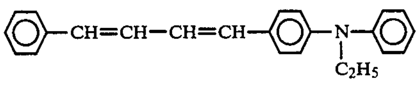 | 2-56 |

TABLE 4-continued

| Synthesis Example No. | Aldehyde | Distyryl Derivative | Compound No. in Table 6 |
|---|---|---|---|
| 2-6 | 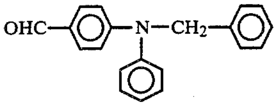 | 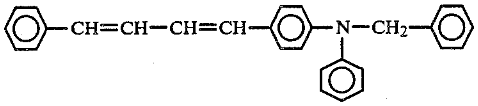 | 2-58 |
| 2-7 | 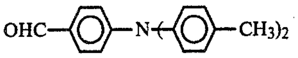 | 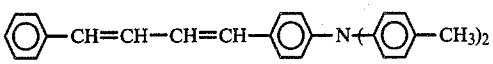 | 2-28 |
| 2-8 | 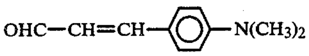 | 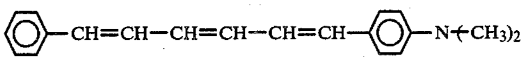 | 2-7 |
| 2-9 | 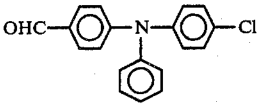 | 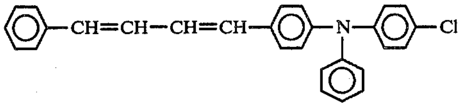 | 2-33 |
| 2-10 | 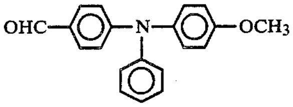 | 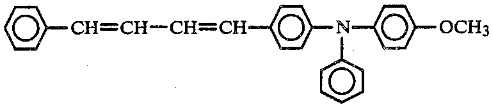 | 2-32 |
| 2-11 | 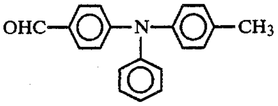 | 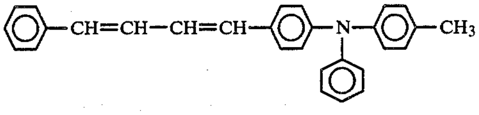 | 2-31 |
| 2-12 | 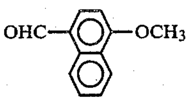 | 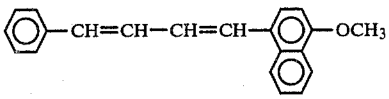 | 2-2 |

TABLE 5

| Synthesis Example No. | Melting Point (°C.) | Elemental Analysis Found/Calculated % C | % H | % N |
|---|---|---|---|---|
| 2-3 | 123.5~124.5 | 86.50/86.58 | 8.49/8.37 | 5.00/5.05 |
| 2-4 | 168.0~169.0 | 89.76/89.72 | 6.71/6.79 | 3.42/3.49 |
| 2-5 | 127.0~127.5 | 88.64/88.56 | 7.24/7.14 | 4.29/4.30 |
| 2-6 | 127.5~128.5 | 89.68/89.87 | 6.61/6.52 | 3.51/3.62 |
| 2-7 | 160.5~161.5 | 89.71/89.72 | 6.69/6.79 | 3.51/3.49 |
| 2-8 | 199.5~201.5 | 87.09/87.21 | 7.72/7.70 | 4.98/5.09 |
| 2-9 | 127.0~128.0 | 82.39/82.43 | 5.46/5.45 | 3.46/3.43 |
| 2-10 | 144.5~145.0 | 86.29/86.31 | 6.27/6.26 | 3.41/3.47 |
| 2-11 | 152.0~153.0 | 89.79/89.87 | 6.53/6.52 | 3.67/3.62 |
| 2-12 | 125.5~126.5 | 88.01/88.07 | 6.37/6.35 | — |

In addition to the distyryl derivatives described in Synthesis Examples 2-1 through 2-12, other distyryl derivatives of the formula (II), listed in the following Table 6, are also useful in the present invention.

(II)

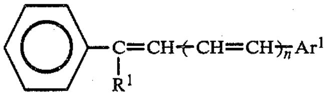

TABLE 6

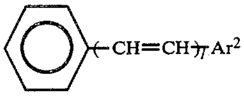

| Compound No. | l | $Ar^2$ |
|---|---|---|
| 2-1 | 2 | 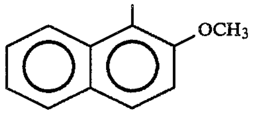 |
| 2-2 | 2 | 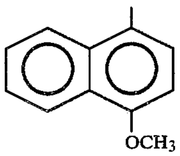 |
| 2-3 | 2 | 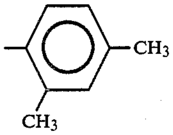 |

TABLE 6-continued
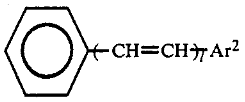
| Compound No. | l | $Ar^2$ |
|---|---|---|
| 2-4 | 2 | 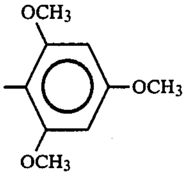 |
| 2-5 | 2 | 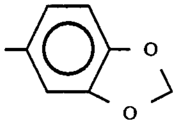 |
| 2-6 | 2 | 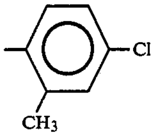 |
| 2-7 | 3 | 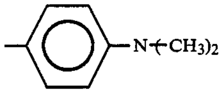 |
| 2-8 | 3 | 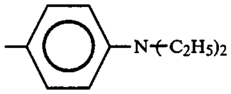 |
| 2-9 | 3 | 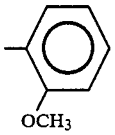 |
| 2-10 | 2 | 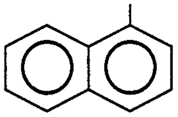 |
| 2-11 | 2 | 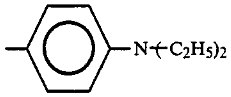 |
| 2-12 | 2 | 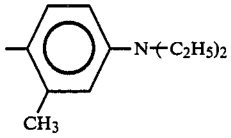 |
| 2-13 | 2 | 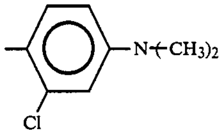 |
TABLE 6-continued
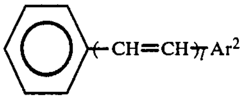
| Compound No. | l | $Ar^2$ |
|---|---|---|
| 2-14 | 2 | 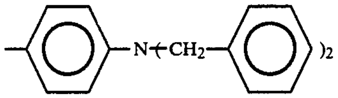 |
| 2-15 | 2 | 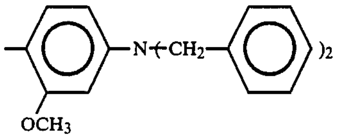 |
| 2-16 | 2 | 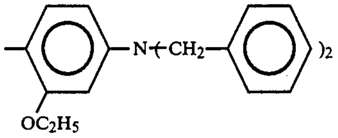 |
| 2-17 | 2 | 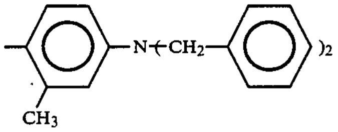 |
| 2-18 | 2 | 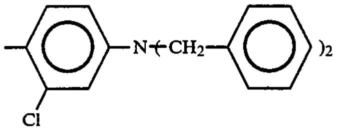 |
| 2-19 | 2 | 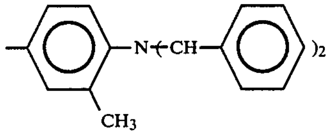 |
| 2-20 | 2 | 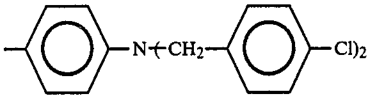 |
| 2-21 | 2 | 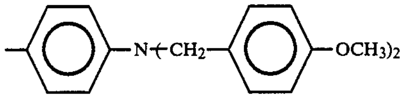 |
| 2-22 | 2 | 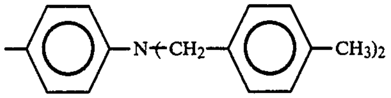 |
| 2-23 | 2 | 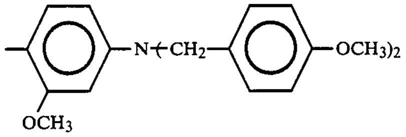 |

TABLE 6-continued
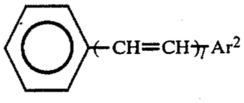
| Compound No. | l | $Ar^2$ |
|---|---|---|
| 2-24 | 2 | 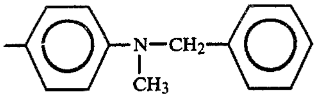 |
| 2-25 | 2 | 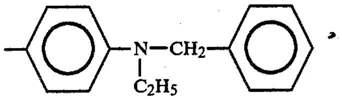 |
| 2-26 | 2 | 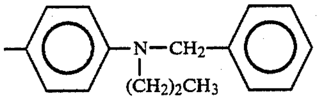 |
| 2-27 | 2 | 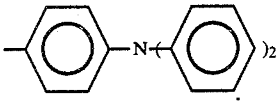 |
| 2-28 | 2 | 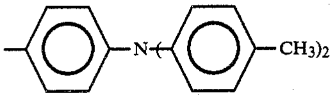 |
| 2-29 | 2 | 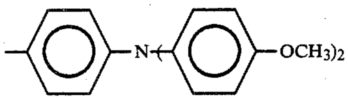 |
| 2-30 | 2 | 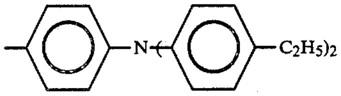 |
| 2-31 | 2 | 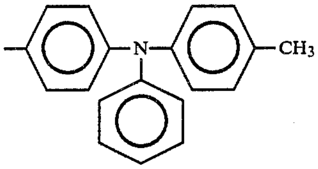 |
| 2-32 | 2 | 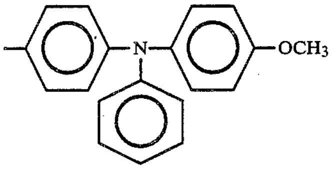 |
| 2-33 | 2 | 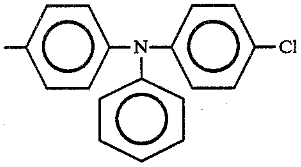 |
TABLE 6-continued
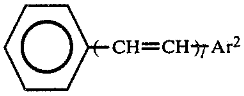
| Compound No. | l | $Ar^2$ |
|---|---|---|
| 2-34 | 2 | 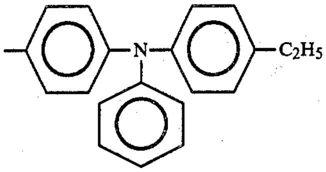 |
| 2-35 | 2 | 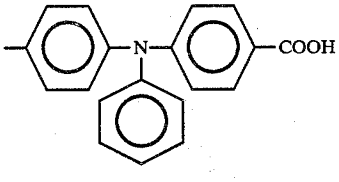 |
| 2-36 | 2 | 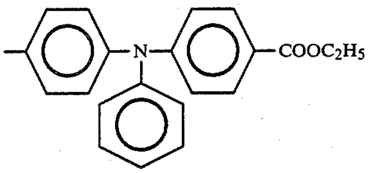 |
| 2-37 | 2 | 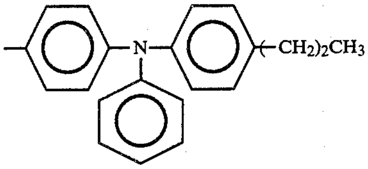 |
| 2-38 | 2 | 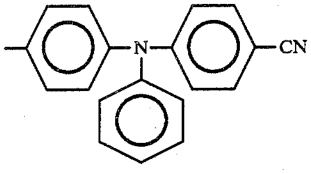 |
| 2-39 | 2 | 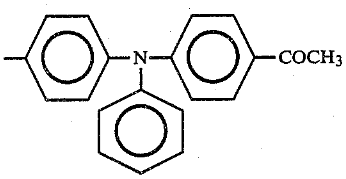 |
| 2-40 | 2 | 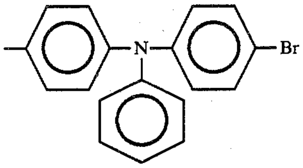 |

TABLE 6-continued
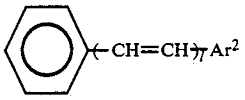
| Compound No. | l | $Ar^2$ |
|---|---|---|
| 2-41 | 2 | 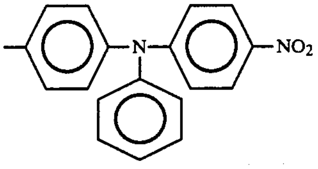 |
| 2-42 | 2 | 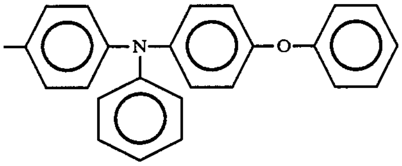 |
| 2-43 | 2 | 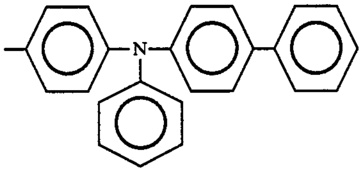 |
| 2-44 | 2 | 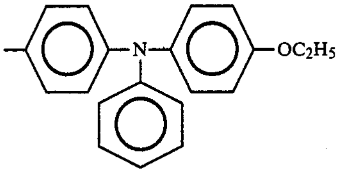 |
| 2-45 | 2 | 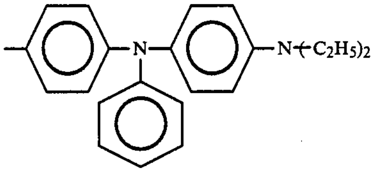 |
| 2-46 | 2 | 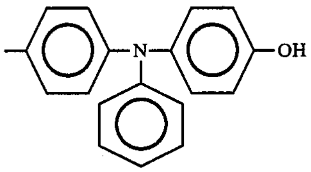 |
| 2-47 | 2 | 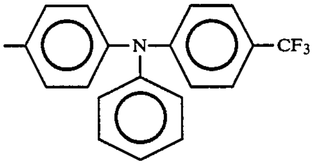 |
TABLE 6-continued
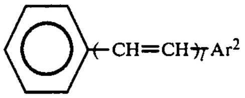
| Compound No. | l | $Ar^2$ |
|---|---|---|
| 2-48 | 2 | 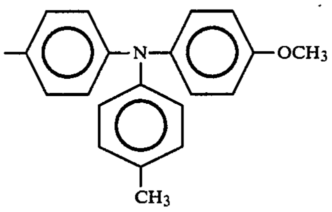 |
| 2-49 | 2 | 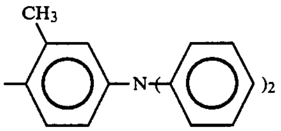 |
| 2-50 | 2 | 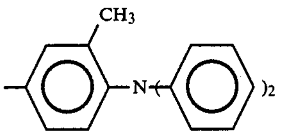 |
| 2-51 | 2 | 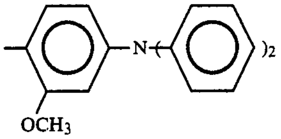 |
| 2-52 | 2 | 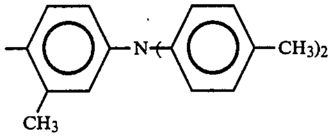 |
| 2-53 | 2 | 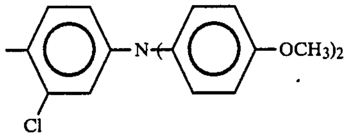 |
| 2-54 | 2 | 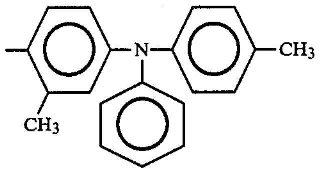 |
| 2-55 | 2 | 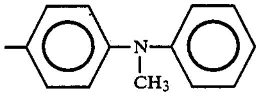 |
| 2-56 | 2 | 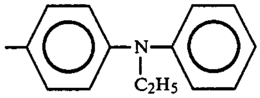 |

TABLE 6-continued

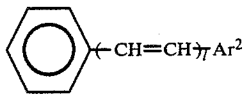

| Compound No. | l | $Ar^2$ |
|---|---|---|
| 2-57 | 2 | 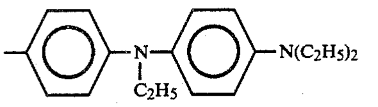 |
| 2-58 | 2 | 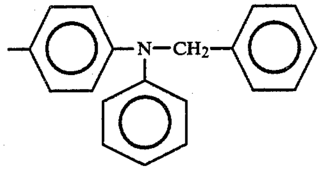 |
| 2-59 | 2 | 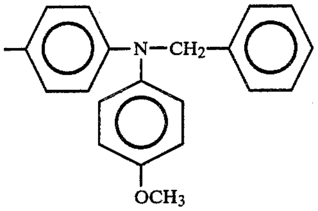 |
| 2-60 | 2 | 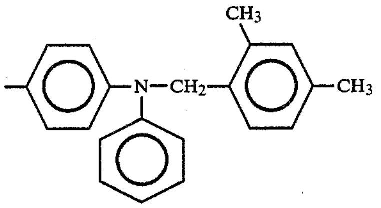 |

When an electrophotographic photoconductor according to the present invention as shown in FIG. 1 is prepared, at least one of the above prepared stilbene derivatives or distyryl derivatives is dispersed in a binder resin solution, and a sensitizer dye is then added to the mixture, and the thus prepared photosensitive liquid is applied to an electroconductive support material 1 and dried, so that a photosensitive layer 2*a* is formed on the electroconductive support material 1.

It is preferable that the thickness of the photosensitive layer 2*a* be in the range of about 3 μm to about 50 μm, more preferably in the range of about 5 μm to about 20 μm. It is preferable that the amount of the stilbene derivative or distyryl contained in the photosensitive layer 2*a* be in the range of about 30 wt.% to about 70 wt.% of the total weight of the photosensitive layer 2*a*, more preferably about 50 wt.% of the total weight of the photosensitive layer 2*a*. Further, it is preferable that the amount of the sensitizer dye contained in the photosensitive layer 2*a* be in the range of about 0.1 wt.% to about 5 wt.% of the total weight of the photosensitive layer 2*a*, more preferably in the range of about 0.5 wt.% to about 3 wt.%, of the total weight of the photosensitive layer 2*a*.

As the sensitizer dye, the following can be employed in the present invention: Triarylmethane dyes, such as Brilliant Green, Victoria Blue B, Methyl Violet, Crystal Violet, and Acid Violet 6B; xanthene dyes, such as Rhodamine B, Rhodamine 6G, Rhodamine G Extra, Eosin S, Erythrosin, Rose Bengale, and Fluorescein; thiazine dyes such as Methylene Blue; cyanin dyes such as cyanin; and pyrylium dyes, such as 2,6-diphenyl-4-(N,N-dimethylaminophenyl)thiapyrylium perchlorate and benzopyrylium salt (as described in Japanese Patent Publication 48-25658). These sensitizer dyes can be used alone or in combination.

An electrophotographic photoconductor according to the present invention as shown in FIG. 2 can be prepared, for example, as follows. A charge generating material 3 in the form of small particles is dispersed in a solution of one or more stilbene derivatives or distyryl derivatives and a binder agent. The thus prepared dispersion is applied to the electroconductive support material 1 and is then dried, whereby a photosensitive layer 2*b* is formed on the electroconductive support material 1.

It is preferable that the thickness of the photosensitive layer 2*b* be in the range of about 3 μm to about 50 μm, more preferably in the range of about 5 μm to about 20 μm. It is preferable that the amount of the stilbene derivative or distyryl derivative contained in the photosensitive layer 2*b* be in the range of about 10 wt.% to about 95 wt.%, more preferably in the range of about 30 wt.% to about 90 wt.% of the total weight of the photosensitive layer 2*b*. Further, it is preferable that the amount of the charge generating material 3 contained in the photosensitive layer 2*b* be in the range of about 0.1 wt.% to about 50 wt.%, more preferably in the range of about 1 wt.% to about 20 wt.%, of the total weight of the photosensitive layer 2*b*.

As the charge generating material 3, the following can be employed in the present invention: inorganic pigments, such as selenium, a selenium-tellurium alloy, cadmium sulfide, a cadmium sulfide-selenium alloy, and α-silicon; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo dye having a distyrylbenzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxazole skeleton (Japanese Laid-Open Patent Application 54-12742), an azo pigment having a fluorenon skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), an azo dye having a distyryl carbazole skeleton (Japanese Laid-Open Patent Application 54-14967); a phthalocyanine-type pigment such as C.I. Pigment Blue 16 (C.I. 74100); Indigo-type pigments such as C.I. Vat Brown 5 (C.I. 73410) and C.I. Vat Dye (C.I. 73030); and perylene-type pigments, such as Algo Scarlet B (made by Bayer Co., Ltd.) and Indanthrene Scarlet R (made by Bayer Co., Ltd). These charge generating materials can be used alone or in combination.

The photoconductor according to the present invention as shown in FIG. 3 can be prepared, for example, as follows. A charge generating material 3 is vacuum-evaporated on the electroconductive support material 1, or a charge generating material 3 in the form of fine particles is dispersed in a solution of a binder agent. This dispersion is applied to the electroconductive support material 1 and then dried, and, if necessary, the applied layer is subjected to buffing to make the surface smooth or to adjust the thickness of the layer to a predetermined thickness, whereby a charge generating layer 5 is formed. A charge transporting layer 6 is then formed on the charge generating layer 5 by applying a solution of one or more stilbene derivatives or distyryl derivatives and a binder agent to the charge generating layer 5 and then drying. In this photoconductor, the charge generating material employed is the same as that employed in the photoconductor shown in FIG. 2.

It is preferable that the thickness of the charge generating layer 5 be less than about 5 μm, more preferably less than about 2 μm. It is preferable that the thickness of the charge transporting layer 6 be in the range of about 3 μm to about 50 μm, more preferably in the range of about 5 μm to about 20 μm. In the case where the charge generating layer 5 comprises the charge generating material 3 in the form of fine particles, dispersed in a binder agent, it is preferable that the amount of the charge generating material 3 in the charge generating layer 5 be in the range of about 10 wt.% to about 95 wt.% of the entire weight of the charge generating layer 5, more preferably in the range of about 50 wt.% to about 90 wt.%. Further, it is preferable that the amount of the stilbene derivative contained in the charge transporting layer 6 be in the range of about 10 wt.% to about 95 wt.%, more preferably in the range of about 30 wt.% to about 90 wt.% of the total weight of the charge transporting layer 6.

As the electroconductive support material 1 for use in the present invention, a metal plate or metal foil, for example, made of aluminum, a plastic film on which a metal, for example, aluminum, is evaporated, or paper which has been treated so as to be electroconductive, can be employed.

As the binder agent for use in the present invention, condensation resins, such as polyamide, polyurethane, polyester, epoxy resin, polyketone and polycarbonate; and vinyl polymers such as polyvinylketone, polystyrene, poly-N-vinylcarbazole and polyacrylamide, can be used.

Other conventional electrically insulating and adhesive resins can be used as the binder agent in the present invention. When necessary, there can be added to the binder resins a plasticizer, for example, halogenated paraffin, polybiphenyl chloride, dimethylnaphthalene and dibutyl phthalate.

In the above described photoconductors according to the present invention, if necessary, an adhesive layer or a barrier layer can be disposed between the electroconductive support material and the photosensitive layer. The adhesive layer or the barrier layer can be made of, for example, polyamide, nitrocellulose or aluminum oxide. It is preferable that the thickness of the adhesive layer or barrier layer be about 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and, when necessary, the developed image can be transferred to a sheet of paper. The photoconductors according to the present invention have high photosensitivity and excellent flexibility.

Preparation of embodiments of an electrophotographic photoconductors according to the present invention will now be explained in detail by referring to the following examples.

EXAMPLE P 1-1

The following components were ground and dispersed in a ball mill to prepare a charge generating layer formation liquid:

| | Parts by Weight |
|---|---|
| Diane Blue (C.I. Pigment Blue 25, C.I. 21180, a charge generating pigment) of the following formula (CG-1) | 76 |
| 2% tetrahydrofuran solution of a polyester resin (Vylon 200 made by Toyobo Co., Ltd.) | 1,260 |
| Tetrahydrofuran | 3,700 |

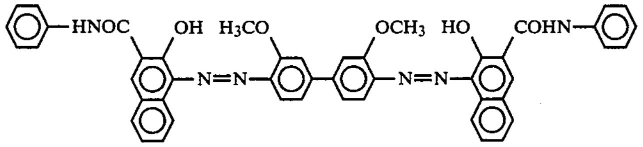

(CG-1)

The thus prepared charge generating layer formation liquid was applied by a doctor blade to the aluminum-evaporated surface of an aluminum-evaporated polyester base film, which served as an electroconductive support material, so that a charge generating layer, with a thickness of about 1 μm when dried at room temperature, was formed on the electroconductive support material.

The following components were then mixed and dissolved, whereby a charge transporting layer formation liquid was prepared:

| | Parts by Weight |
|---|---|
| α-methyl-4'-N,N—diphenylaminostilbene (Prepared in Synthesis Example 1-1, Compound No. 1-26 in Table 3) | 2 |
| Polycarbonate resin (Panlite K 1300 made by Teijin Limited.) | 2 |
| Tetrahydrofuran | 16 |

The thus prepared charge transporting layer formation liquid was applied to the aforementioned charge generating layer by a doctor blade and was dried at 80° C. for 2 minutes and then at 105° C. for 5 minutes, so that a charge transporting layer with a thickness of about 20 μm was formed on the charge generating layer; thus, an electrophotographic photoconductor No. 1-1 according to the present invention was prepared.

The electrophotographic photoconductor No. 1-1 was charged negatively in the dark under application of −6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 4.5 lux, and the exposure $E_{\frac{1}{2}}$ (lux.seconds) required to reduce the initial surface potential Vpo (V) to ½ the initial surface potential Vpo (V) was measured. The results shows that Vpo (V) = −1240 V and $E_{\frac{1}{2}}$ = 2.7 lux.seconds.

EXAMPLES P 1-2 through P 1-33

Example P 1-1 was repeated except that the charge generating material and the charge transporting material (Compound No. 1-26 in Table 3) employed in Example P 1-1 were respectively replaced by the charge generating materials and the charge transporting materials (stilbene derivatives listed in Table 7, whereby electrophotographic photoconductors No. 1-2 through No. 1-33 according to the present invention were prepared.

$V_{po}$ and $E_{\frac{1}{2}}$ of each electrophotographic photoconductor are shown in Table 8.

TABLE 7

| Photoconductor No. | Charge Generating Material | Charge Transporting Material Stilbene Derivative No. in Table 3 |
|---|---|---|
| 1-1 | 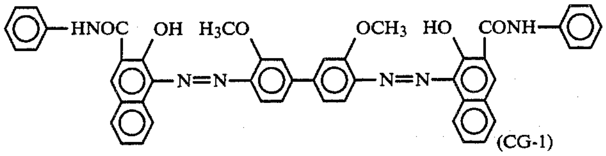 (CG-1) | 1-26 |
| 1-2 | 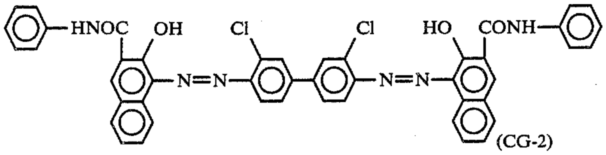 (CG-2) | 1-26 |
| 1-3 | 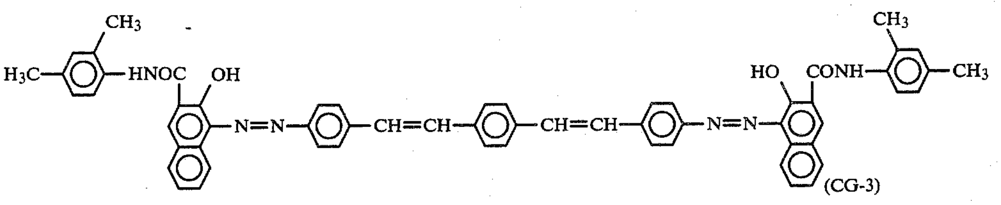 (CG-3) | 1-26 |
| 1-4 | 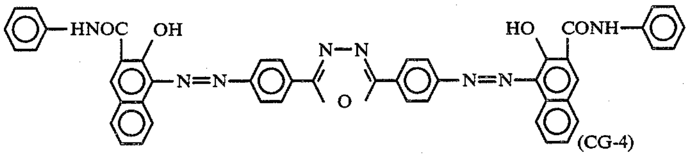 (CG-4) | 1-26 |
| 1-5 | 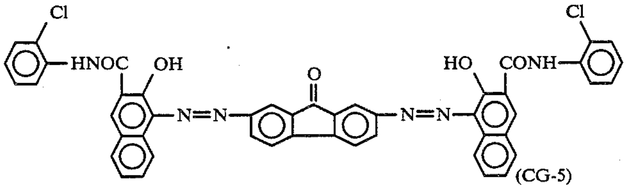 (CG-5) | 1-26 |

TABLE 7-continued
| Photoconductor No. | Charge Generating Material | Charge Transporting Material Stilbene Derivative No. in Table 3 |
|---|---|---|
| 1-6 | 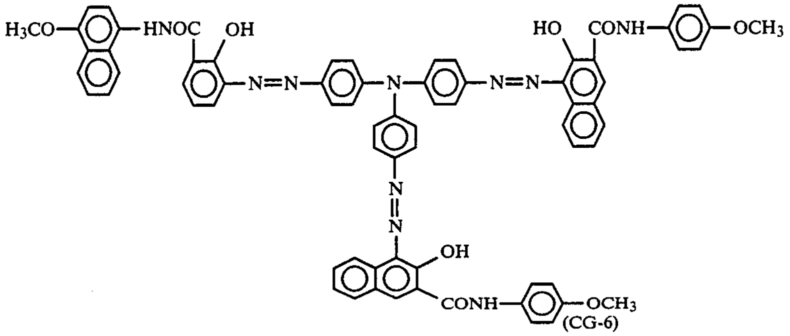 (CG-6) | 1-26 |
| 1-7 | β-Type Copper Phthalocyanine | 1-26 |
| 1-8 | 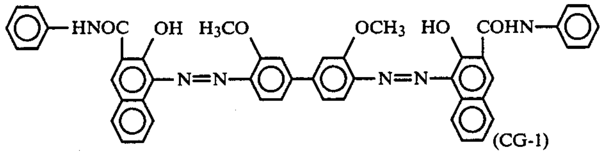 (CG-1) | 1-32 |
| 1-9 | 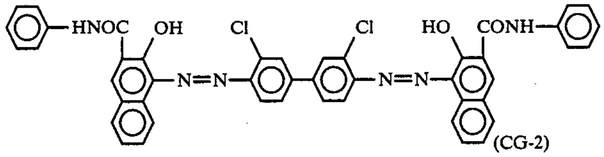 (CG-2) | 1-32 |
| 1-10 | 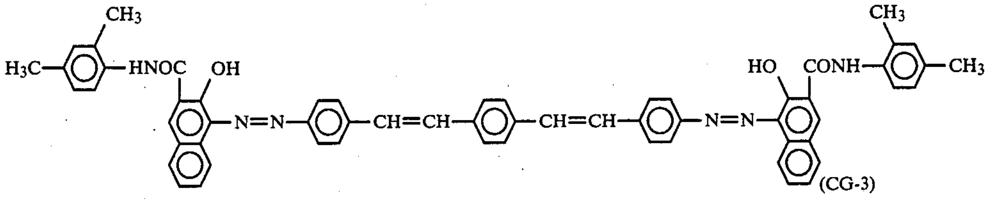 (CG-3) | 1-32 |
| 1-11 | 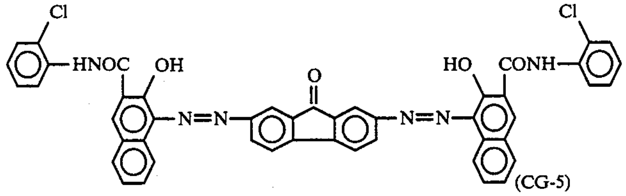 (CG-5) | 1-32 |
| 1-12 | 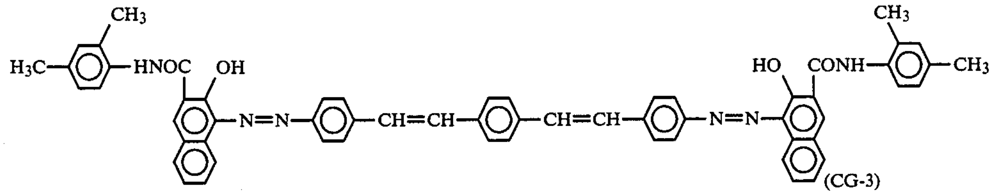 (CG-3) | 1-4 |
| 1-13 | 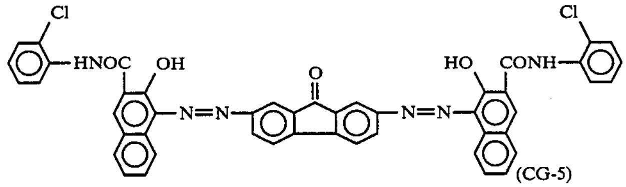 (CG-5) | 1-4 |

TABLE 7-continued
| Photo-con-ductor No. | Charge Generating Material | Charge Trans-porting Material Stilbene Derivative No. in Table 3 |
|---|---|---|
| 1-14 | 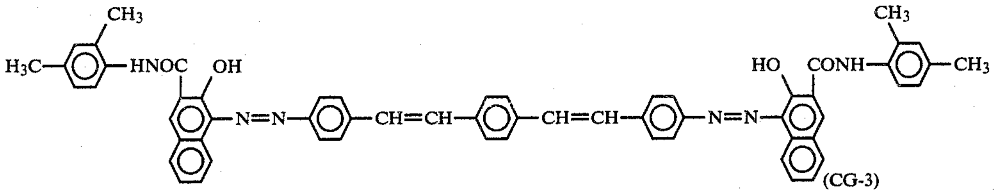 (CG-3) | 1-17 |
| 1-15 | 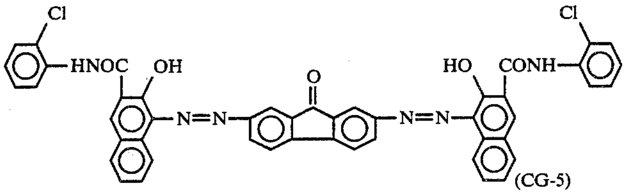 (CG-5) | 1-17 |
| 1-16 | 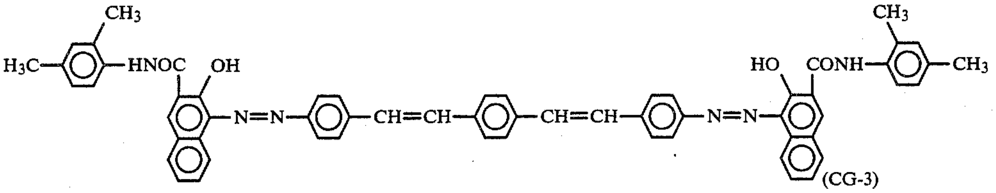 (CG-3) | 1-18 |
| 1-17 | 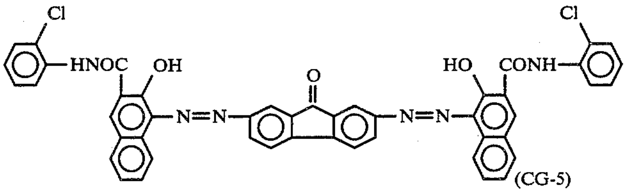 (CG-5) | 1-18 |
| 1-18 | 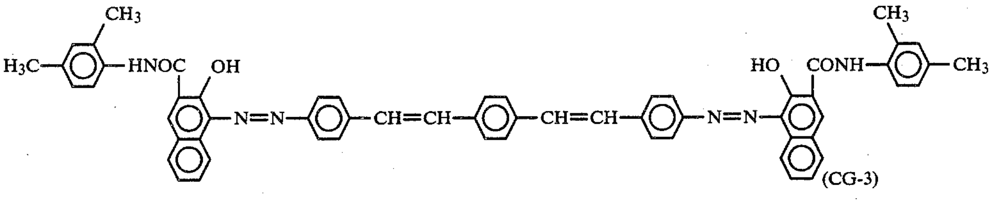 (CG-3) | 1-60 |
| 1-19 | 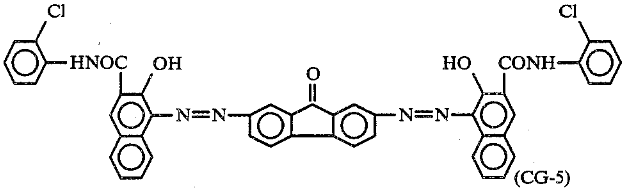 (CG-5) | 1-60 |
| 1-20 | 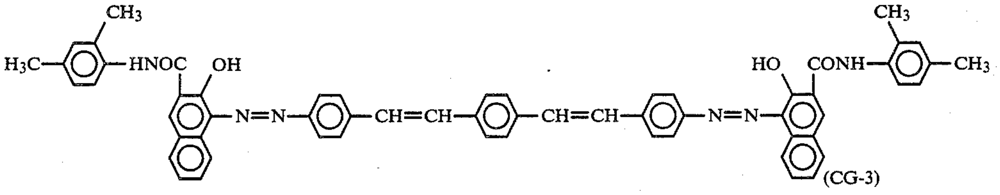 (CG-3) | 1-65 |

TABLE 7-continued
| Photo-conductor No. | Charge Generating Material | Charge Transporting Material Stilbene Derivative No. in Table 3 |
|---|---|---|
| 1-21 | 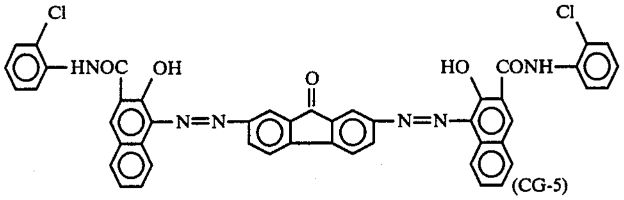 (CG-5) | 1-65 |
| 1-22 | 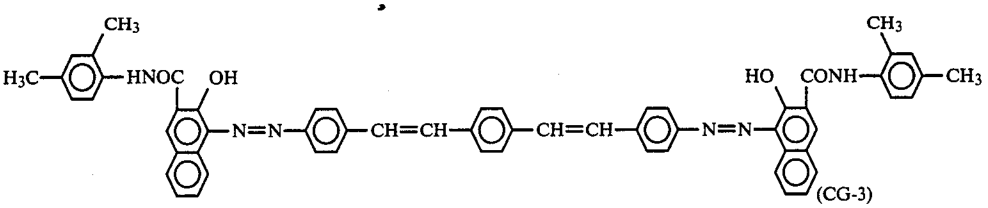 (CG-3) | 1-61 |
| 1-23 | 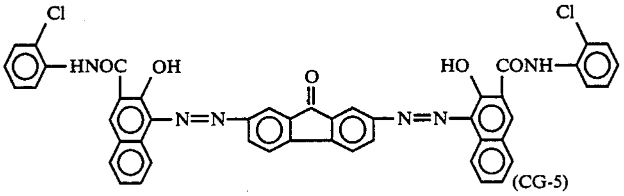 (CG-5) | 1-61 |
| 1-24 | 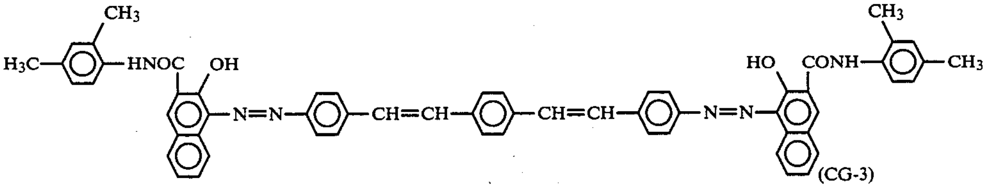 (CG-3) | 1-56 |
| 1-25 | 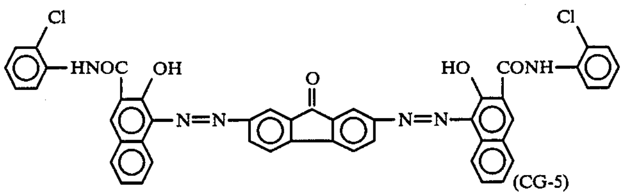 (CG-5) | 1-56 |
| 1-26 | 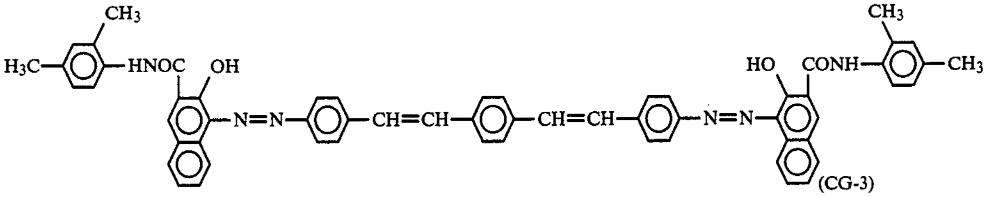 (CG-3) | 1-57 |
| 1-27 | 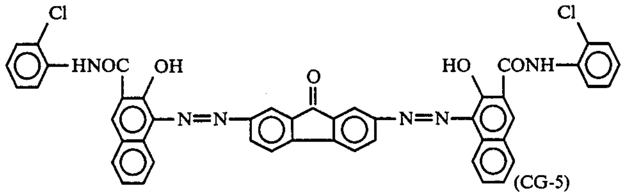 (CG-5) | 1-57 |

TABLE 7-continued

| Photo-conductor No. | Charge Generating Material | Charge Transporting Material Stilbene Derivative No. in Table 3 |
|---|---|---|
| 1-28 | 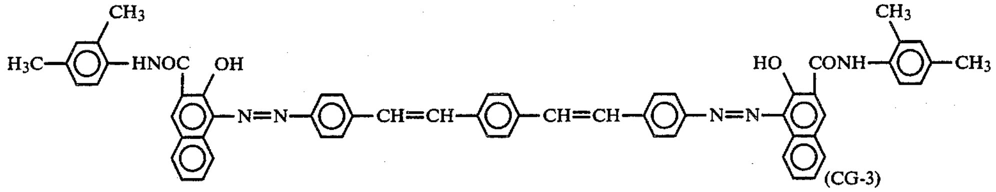 (CG-3) | 1-37 |
| 1-29 | 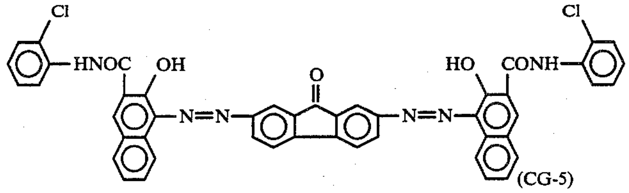 (CG-5) | 1-37 |
| 1-30 | 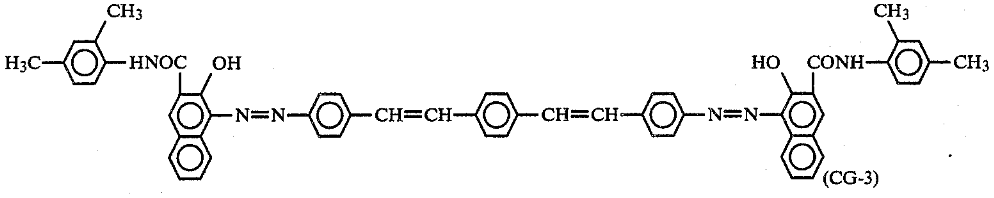 (CG-3) | 1-40 |
| 1-31 | 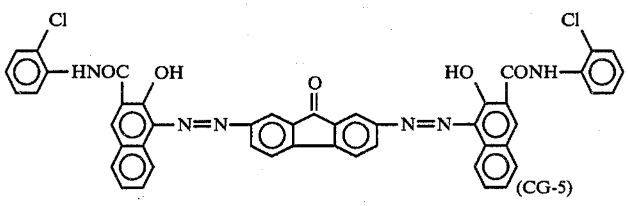 (CG-5) | 1-40 |
| 1-32 | 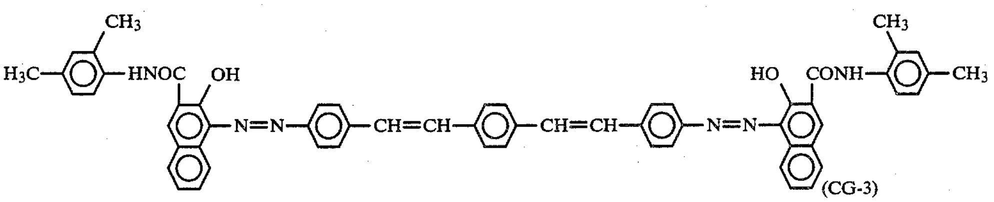 (CG-3) | 1-41 |
| 1-33 | 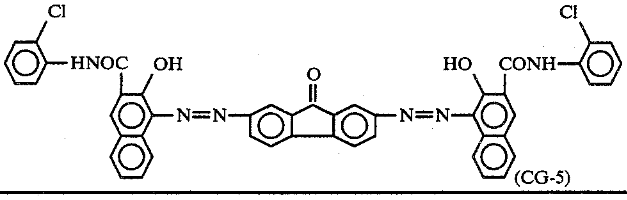 (CG-5) | 1-41 |

EXAMPLE P 1-34

Selenium was vacuum-evaporated with a thickness of approximately 1.0 μm on an approximately 300 μm thick aluminum plate so that a charge generating layer was formed on the aluminum plate.

A charge transporting layer liquid was prepared by mixing and dispersing the following components:

| | Parts by Weight |
|---|---|
| Stilbene Derivative Compound No. 1-26 in Table 3 (prepared in Synthesis Example 1-1, which was the same as that employed in Example P 1-1) | 2 |
| Polyester resin (Polyester Adhesive 49000 made by Du Pont Co.) | 3 |
| Tetrahydrofuran | 45 |

The thus prepared charge transporting layer liquid was applied to the aforementioned selenium charge generating layer by a doctor blade, dried at room temperature and then under reduced pressure, so that a charge transporting layer about 10 μm thick was formed on the charge generating layer; thus, an electrophotographic photoconductor No. 1-34 according to the present invention was prepared.

Vpo and $E_{\frac{1}{2}}$ were measured. The results showed that Vpo = −1410 V and $E_{\frac{1}{2}}$ = 4.1 lux.seconds.

EXAMPLE P 1-35

A perylene pigment C.I. Vat Red 23 (C.I. 71130) of the following formula was vacuum-evaporated with a thickness of about 0.3 μm on an approximately 300 μm thick aluminum plate so that a charge generating layer was formed.

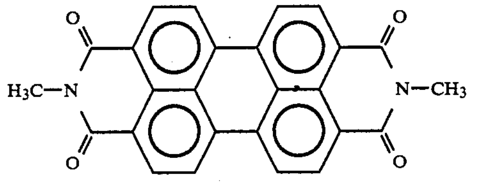

A charge transporting layer liquid was prepared by mixing and dispersing the following components:

| | Parts by Weight |
|---|---|
| Stilbene Derivative Compound No. 1-32 in Table 3 | 2 |
| Polyester resin (Polyester Adhesive 49000 made by Du Pont Co.) | 3 |
| Tetrahydrofuran | 45 |

The thus prepared charge transporting layer liquid was applied to the aforementioned selenium charge generating layer by a doctor blade, dried at room temperature and then dried under reduced pressure, whereby a charge transporting layer about 10 μm thick was formed on the charge generating layer; thus, an electrophotographic photoconductor No. 29 according to the present invention was prepared.

Vpo and $E_{\frac{1}{2}}$ were measured. The results showed that Vpo = −1300 V and $E_{\frac{1}{2}}$ = 5.2 lux.seconds.

EXAMPLE P 1-36

One part by weight of Diane Blue (C.I. Pigment Blue 25, C.I. 21180) which was the same as that employed in Example P 1-1 was added to 158 parts by weight of tetrahydrofuran, and the mixture was ground and dispersed in a ball mill. To this mixture, 12 parts by weight of stilbene derivative No. 1-32 in Table 3 and 18 parts by weight of a polyester resin (Polyester Adhesive 49000 made by Du Pont Co.) were added and mixed, whereby a photosensitive layer formation liquid was prepared.

The thus prepared photosensitive layer formation liquid was applied to an aluminum-evaporated polyester film by a doctor blade and was dried at 100° C. for 30 minutes, so that a photosensitive layer with a thickness of about 16 μm was formed on the aluminum-evaporated polyester film, thus, an electrophotographic conductor No. 1-36 according to the present invention was prepared.

The electrophotographic photoconductor No. 1-36 was charged positively in the dark under application of +6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 4.5 lux, so that the exposure $E_{\frac{1}{2}}$ (lux.seconds) required to reduce the initial surface potential Vpo (V) to ½ the initial surface potential Vpo (V) was measured. The results showed that Vpo (V) = +1210 V and $E_{\frac{1}{2}}$ = 2.9 lux.seconds.

The charge generating material, the charge transporting material, $V_{po}$ and $E_{\frac{1}{2}}$ of each of the electrophotographic photoconductors No. 1-1 through No. 1-36 are summarized in the following Table 8:

TABLE 8

| Photo-Conductor No. | Charge Generating Material | Charge Transporting Material No. (Stilbene Derivative) | $V_{po}$ (V) | $E_{\frac{1}{2}}$ (lux · seconds) |
|---|---|---|---|---|
| 1-1 | CG-1 | 1-26 | −1240 | 2.7 |
| 1-2 | CG-2 | 1-26 | −1120 | 2.5 |
| 1-3 | CG-3 | 1-26 | −1300 | 1.4 |
| 1-4 | CG-4 | 1-26 | −1320 | 4.2 |
| 1-5 | CG-5 | 1-26 | −1205 | 1.3 |
| 1-6 | CG-6 | 1-26 | −1310 | 1.6 |
| 1-7 | β-type Copper Phthalocyanine | 1-26 | −980 | 4.1 |
| 1-8 | CG-1 | 1-32 | −1030 | 2.3 |
| 1-9 | CG-2 | 1-32 | −950 | 2.2 |
| 1-10 | CG-3 | 1-32 | −1180 | 1.0 |
| 1-11 | CG-5 | 1-32 | −890 | 0.8 |
| 1-12 | CG-3 | 1-4 | −1360 | 1.2 |
| 1-13 | CG-5 | 1-4 | −1280 | 1.4 |
| 1-14 | CG-3 | 1-17 | −1600 | 1.4 |
| 1-15 | CG-5 | 1-17 | −1190 | 1.7 |
| 1-16 | CG-3 | 1-18 | −1430 | 1.2 |
| 1-17 | CG-5 | 1-18 | −1220 | 1.4 |
| 1-18 | CG-3 | 1-60 | −1580 | 1.2 |
| 1-19 | CG-5 | 1-60 | −1420 | 3.2 |
| 1-20 | CG-3 | 1-65 | −1260 | 1.1 |
| 1-21 | CG-5 | 1-65 | −1200 | 1.4 |
| 1-22 | CG-3 | 1-61 | −1350 | 1.2 |
| 1-23 | CG-5 | 1-61 | −1240 | 1.3 |
| 1-24 | CG-3 | 1-56 | −1150 | 1.2 |
| 1-25 | CG-5 | 1-56 | −1100 | 1.1 |
| 1-26 | CG-3 | 1-57 | −1200 | 1.3 |
| 1-27 | CG-5 | 1-57 | −1050 | 1.2 |
| 1-28 | CG-3 | 1-37 | −1110 | 1.0 |
| 1-29 | CG-5 | 1-37 | −620 | 0.7 |
| 1-30 | CG-3 | 1-40 | −1210 | 1.1 |
| 1-31 | CG-5 | 1-40 | −690 | 0.7 |
| 1-32 | CG-3 | 1-41 | −1450 | 1.6 |
| 1-33 | CG-5 | 1-41 | −1060 | 1.8 |
| 1-34 | Se | 1-26 | −1410 | 4.1 |
| 1-35 | Perylene Pigment | 1-32 | −1300 | 5.2 |
| 1-36 | CG-1 | 1-32 | +1210 | 2.9 |

Each of the electrophotographic photoconductors prepared in Examples P 1-1 through P 1-35 was negatively charged, while the electrophotographic photoconductor prepared in Example P 1-36 was positively charged, by a commercially available copying machine, so that a latent electrostatic image was formed on each photoconductor and was developed with a dry type developer. The developed images were transferred to a high quality transfer sheet and were fixed to the transfer sheet. As a result, clear images were obtained from each of the electrophotographic photoconductors.

When a wet type developer was used instead of the dry type developer, a clear image was also obtained from each of the electrophotographic photoconductors.

The following are embodiments of electrophotographic photoconductors according to the present invention, in which the distyryl derivatives are employed.

EXAMPLE P 2-1

The following components were ground and dispersed in a ball mill to prepare a charge generating layer formation liquid:

| | Parts by Weight |
|---|---|
| Diane Blue (C.I. Pigment Blue 25, C.I. 21180, a charge generating pigment of the following formula (CG-1)) | 76 |
| 2% tetrahydrofuran solution of a polyester resin (Vylon 200 made by Toyobo Co., Ltd.) | 1,260 |
| Tetrahydrofuran | 3,700 |

(CG-1)

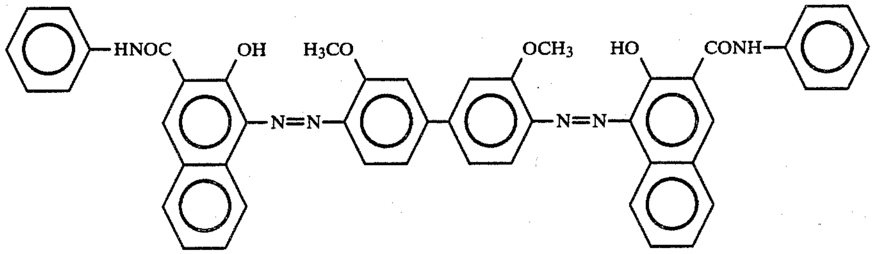

The thus prepared charge generating layer formation liquid was applied by a doctor blade to the aluminum-evaporated surface of an aluminum-evaporated polyester base film, which served as an electroconductive support material, so that a charge generating layer, with a thickness of about 1 μm when dried at room temperature, was formed on the electroconductive support material.

Then the following components were mixed and dissolved, whereby a charge transporting layer formation liquid was prepared:

| | Parts by Weight |
|---|---|
| Distyryl Derivative Compound No. 2-27 in Table 6 | 2 |
| Polycarbonate resin (Panlite K 1300 made by Teijin Limited.) | 2 |
| Tetrahydrofuran | 16 |

The thus prepared charge transporting layer formation liquid was applied to the aforementioned charge generating layer by a doctor blade and was dried at 80° C. for 2 minutes and then at 105° C. for 5 minutes, so that a charge transporting layer with a thickness of about 20 μm was formed on the charge generating layer; thus, an electrophotographic photoconductor No. 2-1 according to the present invention was prepared.

The electrophotographic photoconductor No. 2-1 was charged negatively in the dark under application of −6 kV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 4.5 lux, and the exposure $E_{\frac{1}{2}}$ (lux.seconds) required to reduce the initial surface potential Vpo (V) to ½ the initial surface potential Vpo (V) was measured. The results showed that Vpo (V) = −1110 V and $E_{\frac{1}{2}} = 1.6$ lux.seconds.

EXAMPLES P 2-2 through P 2-27

Example P 2-1 was repeated except that the charge generating material and the charge transporting material (Distyryl Derivative Compound No. 2-27 in Table 6) employed in Example P 2-1 were respectively replaced by the charge generating materials and the charge transporting materials (distyryl derivatives) listed in Table 9, whereby electrophotographic photoconductors No. 2-2 through No. 2-30 according to the present invention were prepared.

$V_{po}$ and $E_{\frac{1}{2}}$ of each electrophotographic photoconductor are also shown in Table 10.

TABLE 9

| Photo-conductor No. | Charge Generating Material | Charge Transporting Material Distyryl Derivative No. in Table 6 |
|---|---|---|
| 2-1 | 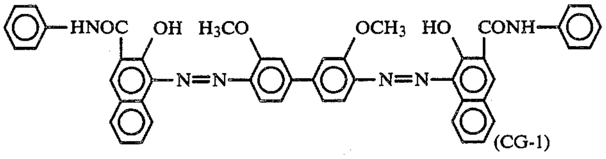 (CG-1) | 2-27 |
| 2-2 | 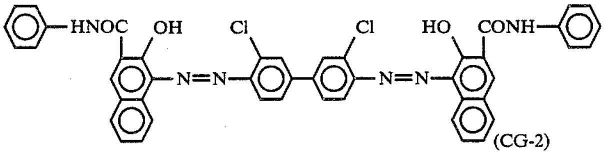 (CG-2) | 2-27 |

TABLE 9-continued
| Photo-conductor No. | Charge Generating Material | Charge Transporting Material Distyryl Derivative No. in Table 6 |
| --- | --- | --- |
| 2-3 | 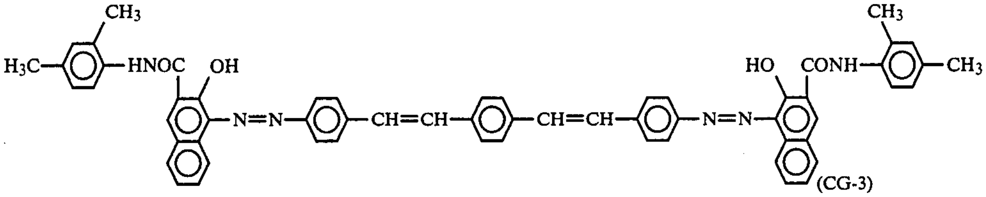 (CG-3) | 2-27 |
| 2-4 | 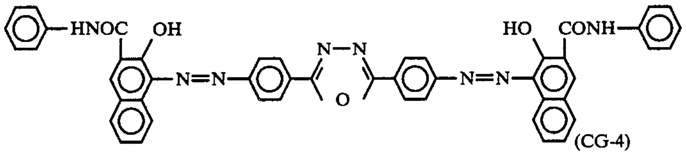 (CG-4) | 2-27 |
| 2-5 | 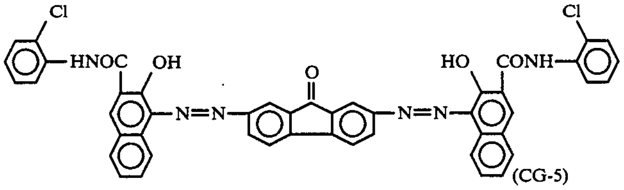 (CG-5) | 2-27 |
| 2-6 | 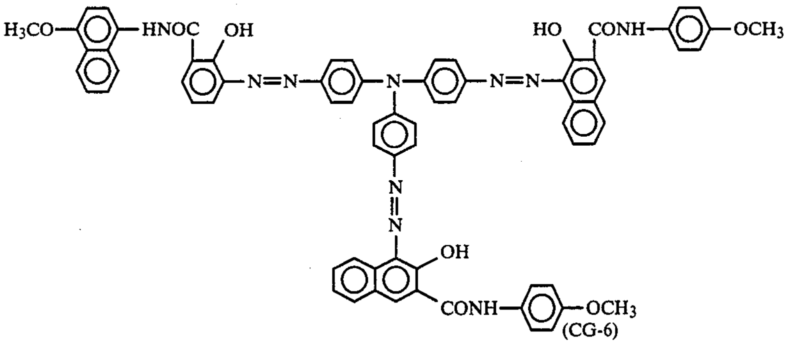 (CG-6) | 2-27 |
| 2-7 | β-type Copper Phthalocyanine | 2-27 |
| 2-8 | 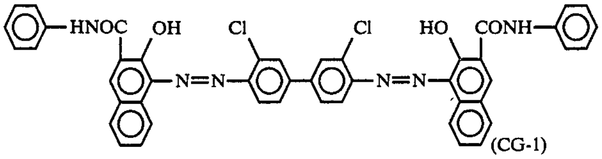 (CG-1) | 2-28 |
| 2-9 | 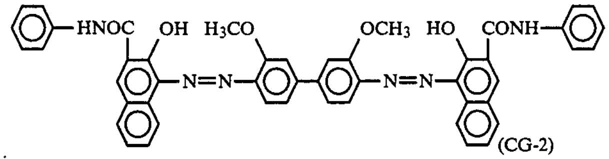 (CG-2) | 2-28 |
| 2-10 | 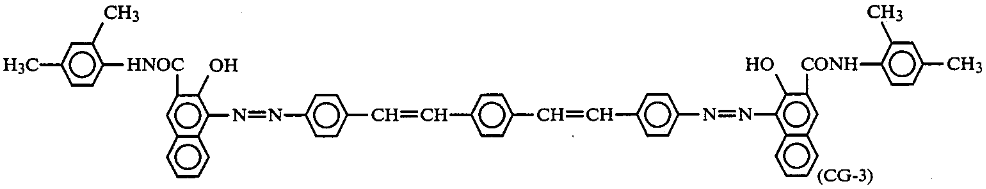 (CG-3) | 2-28 |

TABLE 9-continued
| Photo-conductor No. | Charge Generating Material | Charge Transporting Material Distyryl Derivative No. in Table 6 |
|---|---|---|
| 2-11 | 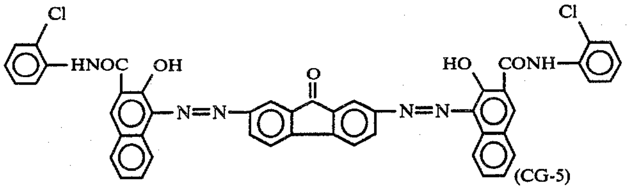 (CG-5) | 2-28 |
| 2-12 | 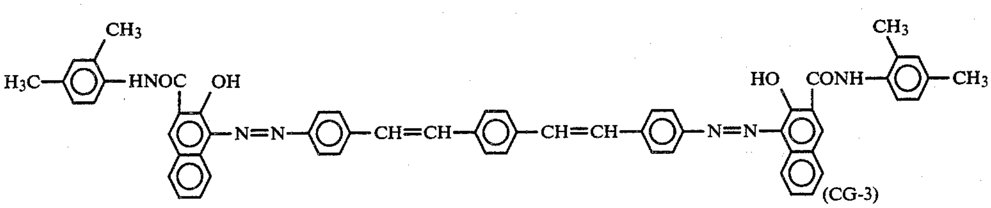 (CG-3) | 2-11 |
| 2-13 | 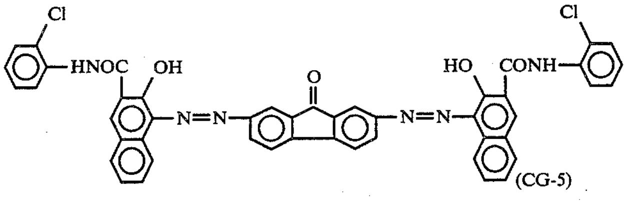 (CG-5) | 2-11 |
| 2-14 | 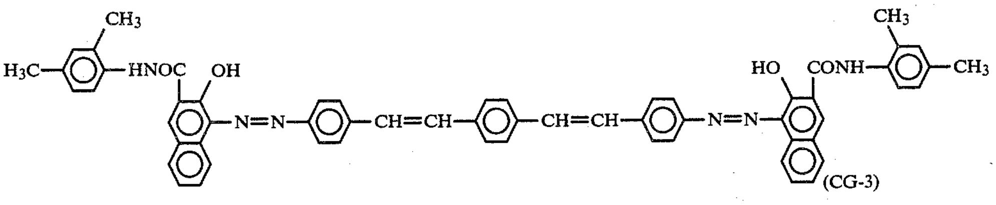 (CG-3) | 2-56 |
| 2-15 | 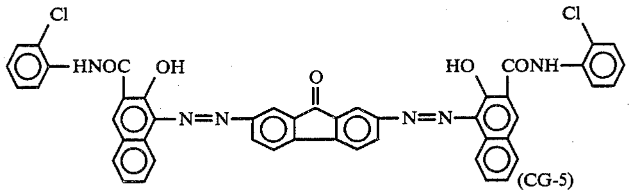 (CG-5) | 2-56 |
| 2-16 | 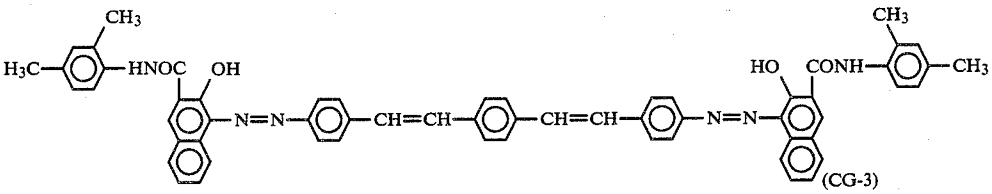 (CG-3) | 2-58 |
| 2-17 | 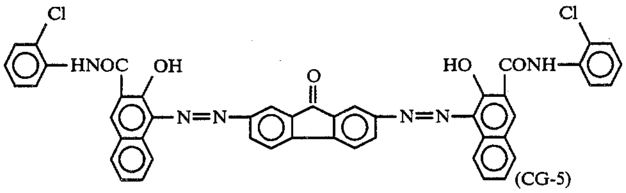 (CG-5) | 2-58 |

TABLE 9-continued
| Photo-conductor No. | Charge Generating Material | Charge Transporting Material Distyryl Derivative No. in Table 6 |
|---|---|---|
| 2-18 | 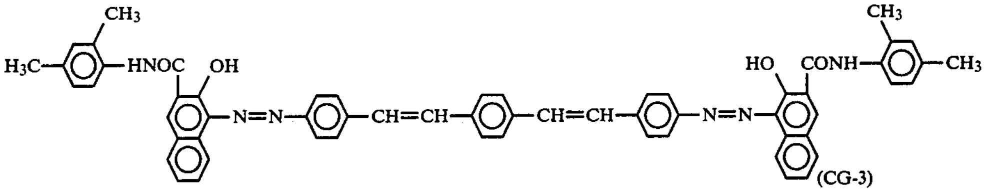 (CG-3) | 2-14 |
| 2-19 | 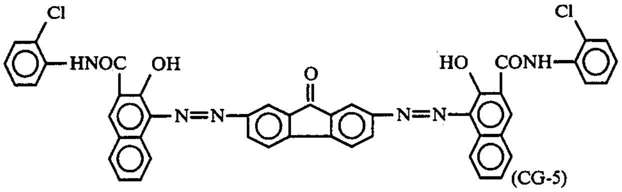 (CG-5) | 2-14 |
| 2-20 | 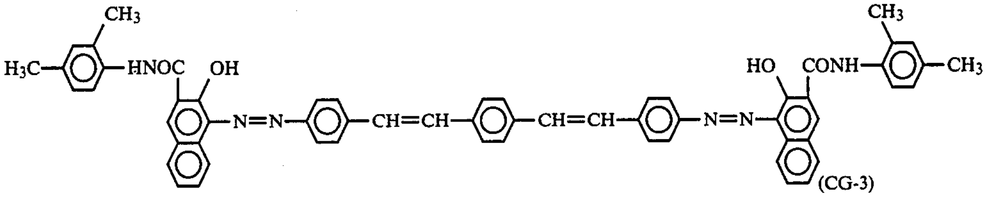 (CG-3) | 2-2 |
| 2-21 | 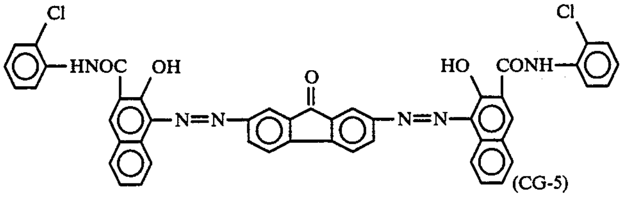 (CG-5) | 2-2 |
| 2-22 | 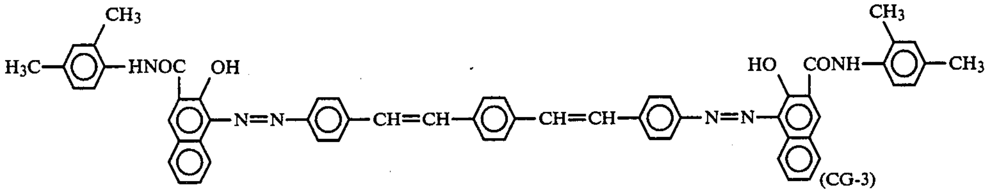 (CG-3) | 2-31 |
| 2-23 | 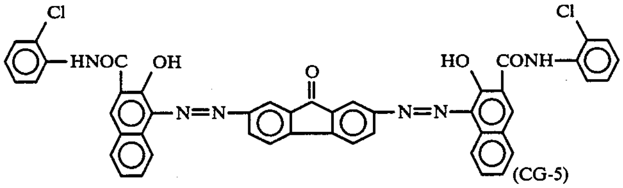 (CG-5) | 2-31 |
| 2-24 | 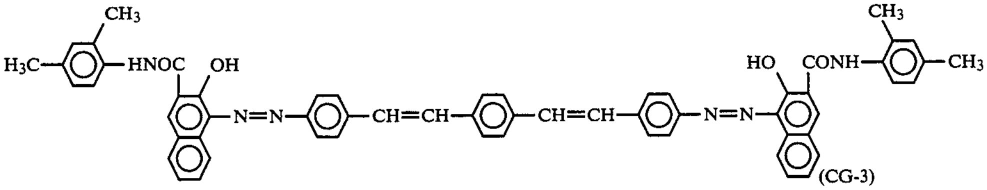 (CG-3) | 2-32 |

TABLE 9-continued

| Photo-con-ductor No. | Charge Generating Material | Charge Transporting Material Distyryl Derivative No. in Table 6 |
|---|---|---|
| 2-25 | 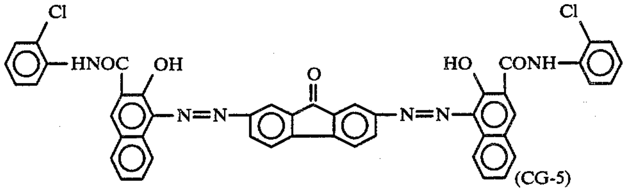 (CG-5) | 2-32 |
| 2-26 | 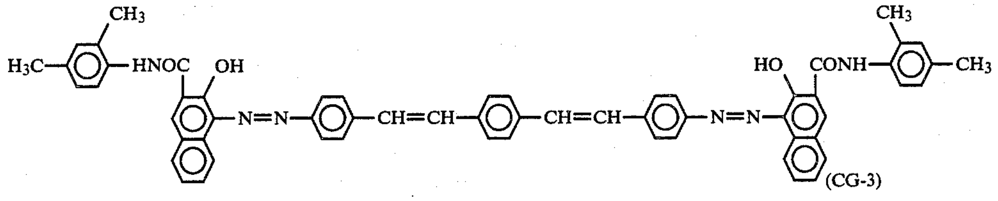 (CG-3) | 2-33 |
| 2-27 | 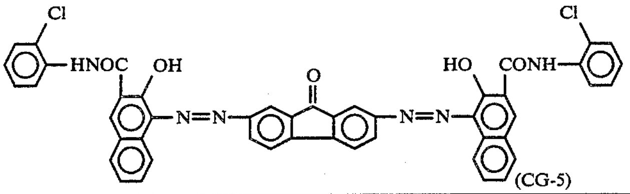 (CG-5) | 2-33 |

EXAMPLE P 2-28

Selenium was vacuum-evaporated with a thickness of approximately 1.0 μm on an approximately 300 μm thick aluminum plate so that a charge generating layer was formed on the aluminum plate.

A charge transporting layer liquid was prepared by mixing and dispersing the following components:

| | Parts by Weight |
|---|---|
| Distyryl Derivative Compound No. 2-27 in Table 6 | 2 |
| Polyester resin (Polyester Adhesive 49000 made by Du Pont Co.) | 3 |
| Tetrahydrofuran | 45 |

The thus prepared charge transporting layer liquid was applied to the aforementioned selenium charge generating layer by a doctor blade, dried at room temperature and then dried under reduced pressure, so that a charge transporting layer about 10 μm thick was formed on the charge generating layer; thus, an electrophotographic photoconductor No. 2-28 according to the present invention was prepared.

Vpo and $E_{1/2}$ were measured. The results showed that Vpo=−1200 V and $E_{1/2}$=2.1 lux.seconds.

EXAMPLE P 2-29

A perylene pigment C.I. Vat Red 23 (C.I. 71130) employed in Example P 2-29 was vacuum-evaporated with a thickness of about 0.3 μm on an approximately 300 μm thick aluminum plate so that a charge generating layer was formed.

A charge transporting layer liquid was prepared by mixing and dispersing the following components:

| | Parts by Weight |
|---|---|
| Distyryl Derivative Compound No. 2-28 in Table 6 | 2 |
| Polyester resin (Polyester Adhesive 49000 made by Du Pont Co.) | 3 |
| Tetrahydrofuran | 45 |

The thus prepared charge transporting layer liquid was applied to the aforementioned selenium charge generating layer by a doctor blade, dried at room temperature and then dried under reduced pressure, whereby a charge transporting layer about 10 μm thick was formed on the charge generating layer; thus, an electrophotographic photoconductor No. 79 according to the present invention was prepared.

Vpo and $E_{178}$ were measured. The results showed that Vpo=−1290 V and $E_{178}$ =3.8 lux.seconds.

EXAMPLE P2-30

One part by weight of Diane Blue (C.I. Pigment Blue 25, C.I. 21180) was added to 158 parts by weight of tetrahydrofuran, and the mixture was ground and dispersed in a ball mill. To this mixture, 12 parts by weight of Distyryl Derivative Compound No. 2-28 in Table 6 and 18 parts by weight of a polyester resin (Polyester Adhesive 49000 made by Du Pont Co.) were added and mixed, whereby a photosensitive layer formation liquid was prepared.

The thus prepared photosensitive layer formation liquid was applied to an aluminum-evaporated polyester film by a doctor blade and was dried at 100° C. for 30 minutes, so that a photosensitive layer with a thickness of about 16 μm was formed on the aluminum-evaporated polyester film, thus, an electrophotographic photoconductor No. 2-30 according to the present invention was prepared.

The electrophotographic photoconductor No. 2-30 was charged positively in the dark under application of +6 KV of corona charge for 20 seconds and was then allowed to stand in the dark for 20 seconds without applying any charge thereto. At this moment, the surface potential Vpo (V) of the photoconductor was measured by a Paper Analyzer (Kawaguchi Electro Works, Model SP-428). The photoconductor was then illuminated by a tungsten lamp in such a manner that the illuminance on the illuminated surface of the photoconductor was 4.5 lux, so that the exposure $E_{178}$ (lux.-seconds) required to reduce the initial surface potential Vpo (V) to ½ the initial surface potential Vpo (V) was measured. The results showed that Vpo (V)=+1200 V and $E_{1/2}$=1.8 lux.seconds.

The charge generating material, the charge transporting material, $V_{po}$ and $E_{178}$ of each of the electrophotographic photoconductors No. 2-1 through No. 2-30 are summarized in the following Table 10:

TABLE 10

| Photo-Conductor No. | Charge Generating Material | Charge Transporting Material No. (Distyryl Derivative) | $V_{po}$ (V) | $E_{1/2}$ (lux · seconds) |
|---|---|---|---|---|
| 2-1 | CG-1 | 2-27 | −1100 | 1.6 |
| 2-2 | CG-2 | 2-27 | −970 | 1.5 |
| 2-3 | CG-3 | 2-27 | −1200 | 1.1 |
| 2-4 | CG-4 | 2-27 | −1150 | 2.2 |
| 2-5 | CG-5 | 2-27 | −800 | 0.8 |
| 2-6 | CG-6 | 2-27 | −1200 | 1.0 |
| 2-7 | β-type Copper Phthalocyanine | 2-27 | −790 | 2.1 |
| 2-8 | CG-1 | 2-28 | −950 | 1.3 |
| 2-9 | CG-2 | 2-28 | −820 | 1.2 |
| 2-10 | CG-3 | 2-28 | −1135 | 1.1 |
| 2-11 | CG-5 | 2-28 | −750 | 0.7 |
| 2-12 | CG-3 | 2-11 | −1380 | 1.2 |
| 2-13 | CG-5 | 2-11 | −600 | 0.8 |
| 2-14 | CG-3 | 2-56 | −1140 | 1.0 |
| 2-15 | CG-5 | 2-56 | −980 | 1.1 |
| 2-16 | CG-3 | 2-58 | −1300 | 1.2 |
| 2-17 | CG-5 | 2-58 | −940 | 1.0 |
| 2-18 | CG-3 | 2-14 | −1390 | 1.2 |
| 2-19 | CG-5 | 2-14 | −990 | 1.1 |
| 2-20 | CG-3 | 2-2 | −1490 | 1.4 |
| 2-21 | CG-5 | 2-2 | −1030 | 1.3 |
| 2-22 | CG-3 | 2-31 | −1140 | 1.2 |
| 2-23 | CG-5 | 2-31 | −920 | 0.8 |
| 2-24 | CG-3 | 2-32 | −830 | 1.2 |
| 2-25 | CG-5 | 2-32 | −680 | 0.9 |
| 2-26 | CG-3 | 2-33 | −1180 | 1.9 |
| 2-27 | CG-5 | 2-33 | −1090 | 1.3 |
| 2-28 | Se | 2-27 | −1200 | 2.1 |
| 2-29 | Perylene Pigment | 2-28 | −1290 | 3.8 |
| 2-30 | CG-1 | 2-28 | +1200 | 1.8 |

Each of the electrophotographic photoconductors prepared in Examples P 2-1 through P 2-29 was negatively charged, while the electrophotographic photoconductor prepared in Example P 2-30 was positively charged, by a commercially available copying machine, so that latent electrostatic images were formed on each photoconductor and were developed with a dry type developer. The developed images were transferred to a high quality transfer sheet and were fixed to the transfer sheet. As a result, clear images were obtained from each of the electrophotographic photoconductors.

What is claimed is:

1. A stilbene derivative of the formula

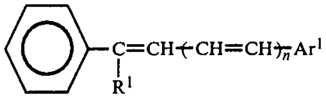

wherein $R^1$ represents an alkyl group or an aralkyl group, $Ar^1$ represents

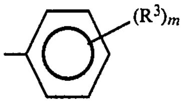

in which $R^3$ independently represents hydrogen, an alkyl group, an alkoxy group, halogen or a substituted amino group represented by

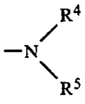

wherein $R^4$ and $R^5$ each represent an alkyl group, an unsubstituted or substituted aralkyl group, or an unsubstituted or substituted aryl group, with the proviso that at least one of $R^4$ and $R^5$ is unsubstituted aralkyl, substituted aralkyl, unsubstituted aryl or substituted aryl, m is an integer of 1, 2 or 3, with the proviso that one $R^3$ is

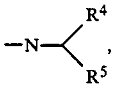, and when m is an integer of 2 or 3, $R^3$'s may be the same or different, and n is an integer of 0 or 1.

2. A distyryl derivative of the formula

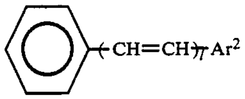

wherein $Ar^2$ represents

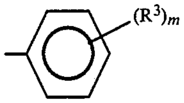

in which $R^3$ independently represents hydrogen, an alkyl group, an alkoxy group, halogen or a substituted amino group represented by

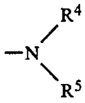

wherein $R^4$ and $R^5$ each represent an alkyl group, an unsubstituted or substituted aralkyl group, or an unsubstituted or substituted aryl group, with the proviso that at least one of $R^4$ and $R^5$ is unsubstituted aralkyl, substituted aralkyl, unsubstituted aryl or substituted aryl, m is an integer of 1, 2 or 3, with the proviso that one $R^3$ is

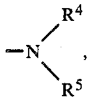, and when m is an integer of 2 or 3, $R^3$'s may be the same or different, and l is an integer of 2 or 3.

3. A stilbene derivative as claimed in claim 1, wherein the specific combination of constituents $R^1$, n and $Ar^1$ are selected from the group consisting of:

| $R^1$ | n | $Ar^1$ |
|---|---|---|
| $-CH_3$ | 0 | 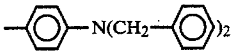 |
| $-CH_3$ | 0 | 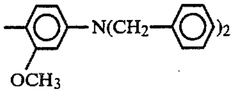 |
| $-CH_3$ | 0 | 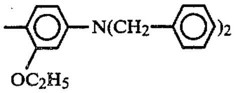 |
| $-CH_3$ | 0 | 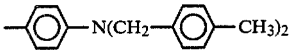 |
| $-CH_3$ | 0 | 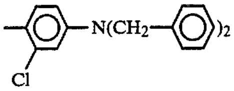 |
| $-CH_3$ | 0 | 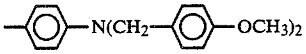 |
| $-CH_3$ | 0 | 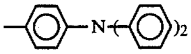 |
| $-C_2H_5$ | 0 | 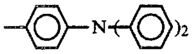 |
| $-C_3H_7(n)$ | 0 | 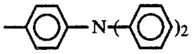 |
| $-C_3H_7(i)$ | 0 | 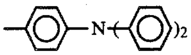 |
| $-C_4H_3(n)$ | 0 | 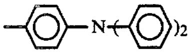 |
| 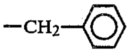 | 0 | 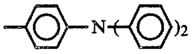 |
| $-CH_3$ | 0 | 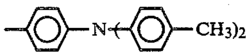 |
| $-C_2H_5$ | 0 | 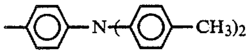 |
| 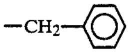 | 0 | 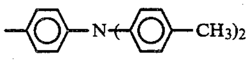 |

-continued

| $R^1$ | n | $Ar^1$ |
|---|---|---|
| $-CH_3$ | 0 | 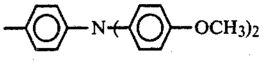 |
| $-CH_3$ | 0 | 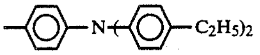 |
| $-CH_3$ | 0 | 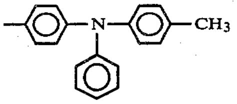 |
| $-C_2H_5$ | 0 | 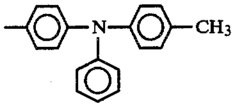 |
| 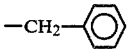 | 0 | 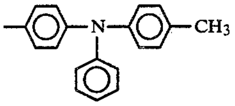 |
| $-CH_3$ | 0 | 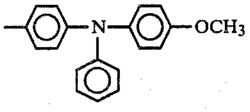 |
| $-CH_3$ | 0 | 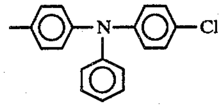 |
| $-CH_3$ | 0 | 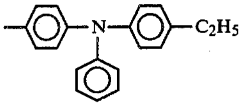 |
| $-CH_3$ | 0 | 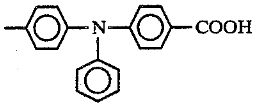 |
| $-CH_3$ | 0 | 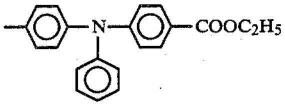 |
| $-CH_3$ | 0 | 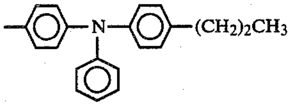 |
| $-CH_3$ | 0 | 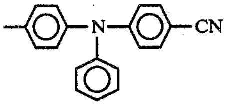 |
| $-CH_3$ | 0 | 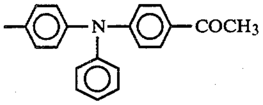 |

-continued
| $R^1$ | n | $Ar^1$ |
|---|---|---|
| $-CH_3$ | 0 | 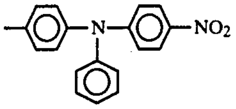 |
| $-CH_3$ | 0 | 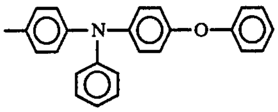 |
| $-CH_3$ | 0 | 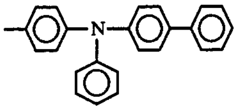 |
| $-CH_3$ | 0 | 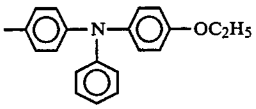 |
| $-CH_3$ | 0 | 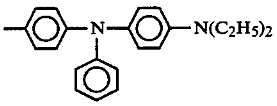 |
| $-CH_3$ | 0 | 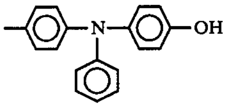 |
| $-CH_3$ | 0 | 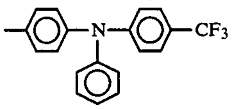 |
| $-CH_3$ | 0 | 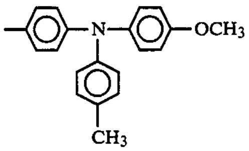 |
| $-CH_3$ | 0 | 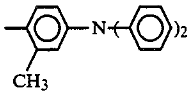 |
| $-CH_3$ | 0 | 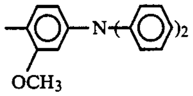 |
| $-CH_3$ | 0 | 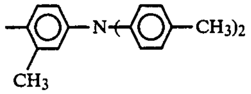 |
| $-CH_3$ | 0 | 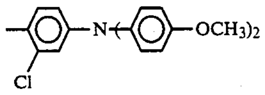 |
-continued
| $R^1$ | n | $Ar^1$ |
|---|---|---|
| $-CH_3$ | 0 | 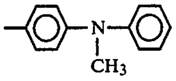 |
| $-CH_3$ | 0 | 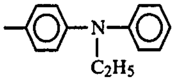 |
| $-CH_3$ | 0 | 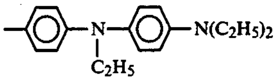 |
| $-C_2H_5$ | 0 | 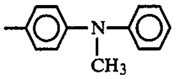 |
| $-C_2H_5$ | 0 | 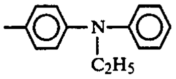 |
| $-CH_3$ | 0 | 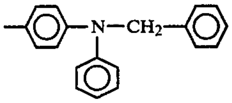 |
| $-C_2H_5$ | 0 | 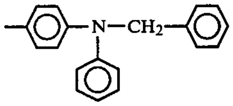 |
| $-CH_3$ | 0 | 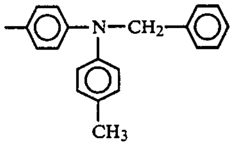 |
| $-CH_3$ | 0 | 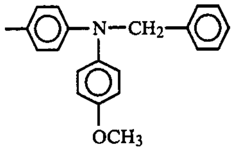 |
| $-CH_3$ | 0 | 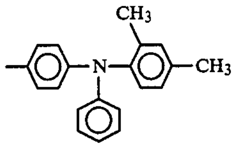 |
| $-CH_3$ | 0 | 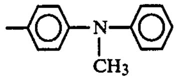 |
4. A compound as claimed in claim 1, which has the formula
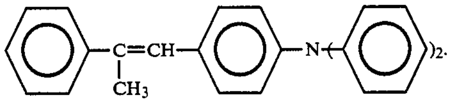

5. A compound as claimed in claim 1 in which both of $R^4$ and $R^5$ are selected from the group consisting of unsubstituted aralkyl, substituted aralkyl, unsubstituted aryl and substituted aryl.

6. A compound as claimed in claim 5 in which the substituents for substituted aralkyl and substituted aryl are selected from the group consisting of alkyl, alkoxy, thioalkoxy, thiophenoxy, halogen, dialkylamino, hydroxy, carboxyl and ester thereof, acyl, allyloxy, aralkyloxy, trihalomethyl and cyano.

7. A compound as claimed in claim 1 in which one of $R^4$ and $R^5$ is selected from the group consisting of unsubstituted aralkyl, substituted aralkyl, unsubstituted aryl and substituted aryl and the other of $R^4$ and $R^5$ is alkyl.

8. A compound as claimed in claim 7 in which the substituents for substituted aralkyl and substituted aryl are selected from the group consisting of alkyl, alkoxy, thioalkoxy, thiophenoxy, halogen, dialkylamino, hydroxy, carboxyl and ester thereof, acyl, allyloxy, aralkyloxy, trihalomethyl and cyano.

9. A compound as claimed in claim 2 in which the substituents for substituted aralkyl and substituted aryl are selected from the group consisting of alkyl, alkoxy, thioalkoxy, thiophenoxy, halogen, dialkylamino, hydroxy, carboxyl and ester thereof, acyl, allyloxy, aralkyloxy, trihalomethyl, nitro and cyano.

10. A compound as claimed in claim 1 in which $R^4$ and $R^5$ are selected from the group consisting of methyl, ethyl, benzyl, phenyl, p-methylphenyl, p-ethylphenyl, p-propylphenyl, p-chlorophenyl, p-methoxyphenyl, (4-methylphenyl)methyl, (4-methoxyphenyl)methyl, p-carboxyphenyl, (4-carbonylethoxy)-phenyl, p-cyanophenyl, p-acetylphenyl, p-nitrophenyl, p-phenoxyphenyl, 4-biphenylyl, p-ethoxyphenyl, p-diethylaminophenyl, p-hydroxyphenyl, p-trifluoromethylphenyl and 2,4-dimethylphenyl.

11. A compound as claimed in claim 2 in which $R^4$ and $R^5$ are selected from the group consisting of methyl, ethyl, propyl, benzyl, phenyl, p-methylphenyl, p-chlorophenyl, p-methoxyphenyl, (4-chlorophenyl)-methyl, (4-methoxyphenyl)methyl, (4-methylphenyl)-methyl, p-ethylphenyl, p-carboxyphenyl, p-carbonylethoxyphenyl, p-propylphenyl, p-cyanophenyl, p-acetylphenyl, p-bromophenyl, p-nitrophenyl, p-phenoxyphenyl, 4-biphenylyl, p-ethoxyphenyl, p-diethylaminophenyl, p-hydroxyphenyl, p-trifluoromethylphenyl and 2,4-dimethylphenyl.

* * * * *